United States Patent
Martin

(10) Patent No.: US 12,121,595 B2
(45) Date of Patent: Oct. 22, 2024

(54) METHODS AND MATERIALS FOR GALGT2 GENE THERAPY

(71) Applicant: RESEARCH INSTITUTE AT NATIONWIDE CHILDREN'S HOSPITAL, Columbus, OH (US)

(72) Inventor: Paul Taylor Martin, Columbus, OH (US)

(73) Assignee: RESEARCH INSTITUTE AT NATIONWIDE CHILDREN'S HOSPITAL, Columbus, OH (US)

( * ) Notice: Subject to any disclaimer, the term of this patent is extended or adjusted under 35 U.S.C. 154(b) by 447 days.

(21) Appl. No.: 17/203,232

(22) Filed: Mar. 16, 2021

(65) Prior Publication Data

US 2021/0220484 A1 Jul. 22, 2021

Related U.S. Application Data

(63) Continuation of application No. 15/759,474, filed as application No. PCT/US2016/052051 on Sep. 16, 2016, now Pat. No. 10,980,897.

(60) Provisional application No. 62/301,260, filed on Feb. 29, 2016, provisional application No. 62/221,068, filed on Sep. 20, 2015, provisional application No. 62/220,107, filed on Sep. 17, 2015.

(51) Int. Cl.
*C12N 15/86* (2006.01)
*A61K 38/45* (2006.01)
*A61K 48/00* (2006.01)
*A61P 21/00* (2006.01)
*C12N 9/10* (2006.01)
*C12Q 1/68* (2018.01)
*C07H 21/04* (2006.01)
*C12N 15/864* (2006.01)

(52) U.S. Cl.
CPC .......... *A61K 48/0058* (2013.01); *A61K 38/45* (2013.01); *A61K 48/0075* (2013.01); *A61P 21/00* (2018.01); *C12N 9/1048* (2013.01); *C12N 9/1051* (2013.01); *C12N 15/86* (2013.01); *C12Q 1/68* (2013.01); *C12Y 204/01165* (2013.01); *C07H 21/04* (2013.01); *C12N 15/8645* (2013.01); *C12N 2750/14143* (2013.01); *C12N 2830/008* (2013.01); *C12N 2830/42* (2013.01)

(58) Field of Classification Search
CPC .. A61K 48/005; A61K 48/0075; A61K 38/45; C12N 15/86; C12N 15/8645; C12N 2750/14143; C12N 2830/42; C07H 21/04
See application file for complete search history.

(56) References Cited

U.S. PATENT DOCUMENTS

| 5,173,414 A | 12/1992 | Lebkowski et al. |
| 5,658,776 A | 8/1997 | Flotte et al. |
| 5,786,211 A | 7/1998 | Johnson |
| 5,871,982 A | 2/1999 | Wilson et al. |
| 6,258,595 B1 | 7/2001 | Gao et al. |
| 6,566,118 B1 | 5/2003 | Atkinson et al. |
| 9,434,928 B2 | 9/2016 | Mendell et al. |
| 2006/0194265 A1 | 8/2006 | Morris et al. |
| 2015/0045416 A1 | 2/2015 | Mitrani-Rosenbaum et al. |

FOREIGN PATENT DOCUMENTS

| CN | 104520428 A | 4/2015 |
| WO | 1995/13365 A1 | 5/1995 |
| WO | 1995/13392 A1 | 5/1995 |
| WO | 1996/17947 A1 | 6/1996 |
| WO | 1997/06243 A1 | 2/1997 |
| WO | 1997/08298 A1 | 3/1997 |
| WO | 1997/09441 A2 | 3/1997 |
| WO | 1997/21825 A1 | 6/1997 |
| WO | 1998/09657 A2 | 3/1998 |
| WO | 1999/11764 A2 | 3/1999 |
| WO | 2001/83692 A2 | 11/2001 |
| WO | 2013/078316 A1 | 5/2013 |
| WO | 2017/049031 A1 | 3/2017 |

OTHER PUBLICATIONS

Johns Hopkins Medicine, 2023 (Types of Muscular Dystrophy and Neuromuscular diseases, p. 1-6).*
Kotterman et al., 2014 (Nature Reviews, vol. 15, p. 445-451).*
Shim et al., 2017 (Current Gene Therapy, vol. 17, No. 5, p. 1-18).*
Lenzi et al., 2014 (NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16) .*
Bulcha et al., 2021 (Signal Transduction and Targeted Therapy, 6:53, p. 1-24).*
GenBank: Accession No. AF510036.1, Homo sapiens beta-4-N-acetylgalactosaminyltransferase mRNA, complete cds, Dec. 5, 2023.
Presti et al., Molecular Cloning of the Human beta1, 4 N-Acetylgalactosaminyltrans-ferase Responsible for the Biosynthesis of the Sda Histo-Blood Group Antigen: The Sequence Predicts a Very long Cytoplasmic Domain, J. Biochem, 134:675-682 (2003).
Wang et al., Construction and analysis of compact muscle-specific promoters for AAV vectors, Gene Therapy, 15:1489-1499 (2008).

(Continued)

Primary Examiner — Shin Lin Chen
(74) Attorney, Agent, or Firm — MARSHALL, GERSTEIN & BORUN LLP

(57) ABSTRACT

The present disclosure relates to recombinant adeno-associated virus (rAAV) delivery of a GALGT2 polynucleotide. The disclosure provides rAAV and methods of using the rAAV for GALGT2 gene therapy of neuromuscular disorders. Exemplary neuromuscular disorders include, but are not limited to, muscular dystrophies such as Duchenne muscular dystrophy, Congenital Muscular Dystrophy 1A and Limb Girdle Muscular Dystrophy 2D.

17 Claims, 1 Drawing Sheet

Specification includes a Sequence Listing.

(56) References Cited

OTHER PUBLICATIONS

Genbank Accession No. AJ517771.1, Homo sapiens partial mRNA for sda beta-1,4-GalNAc transferase (GALGT2 gene), splice variant 2, Oct. 7, 2008.
Keiya Ozaway, Gene therapy using AAV vectors, Drug Delivery System, 22(6):643-650 (2007).
Bengtsson, et al., Progress and prospects of gene therapy clinical trials for the muscular dystrophies, Human Molecular Genetics., 25:R9-R17 (2016).
Carter et al., Adeno-associated virus vectors, Current Opinion in Biotechnology., 3:533-539 (1992).
Chalberg et al., GeneSeq Accession No. BAY70796, computer printout, 7-8 (2013).
Chamberlain et al., Geneseq accession No. AAL44606, Computer printout, 8-9 (2002).
Chandrasekharan et al., Genetic defects in muscular dystrophy, Methods Enzymol., 479:291-322 (2010).
Chicoin et al., Neuromuscular Therapeutic Strategies: Overcoming the Barriers from Microscope to Marketplace, Muscular Dystrophy Association National Scientific Conference, Mar. 13-16, 2011, Las Vegas, Nevada (Abstract Only).
Chicoine et al., Plasmapheresis Eliminates the Negative Impact of AAV Antibodies on Microdystrophin Gene Expression Following Vascular Delivery, Mol Ther., 22(2):338-347 (2014).
Chicoine et al., Vascular Delivery of rAAVrh74.MCK.GALGT2 to the Gastrocnemius Muscle of the Rhesus Macaque Stimulates the Expression of Dystrophin and Laminin a2 Surrogates, Mol. Ther., 22(4):713-724 (2014).
Clark et al., A stable cell line carrying adenovirus-inducible rep and cap genes allows for infectivity titration of adeno-associated virus vectors, Gene Ther., 3:1124-32 (1996).
Clark et al., Highly purified recombinant adeno-associated virus vectors are biologically active and free of detectable helper and wild-type viruses, Hum. Gene. Ther., 10:1031-9 (1999).
Cserjesi et al., Myogenin induces the myocyte-specific enhancer binding factor MEF-2 independently of other muscle-specific gene products, Mol. Cell Biol., 11:4854-62 (1991).
De et al., High levels of persistent expression of alpha1-antitrypsin mediated by the nonhuman primate serotype rh.10 adeno-associated virus despite preexisting immunity to common human adeno-associated viruses, Mol. Ther., 13:67-76 (2006).
Degroote et al., B4GALNT2 Gene Expression Controls the Biosynthesis of Sda and Sialyl Lewis X Antigens in Healthy and Cancer Human Gastrointestinal Tract, Int. J. Bio. Cell. Bio., 53:442-449 (2014).
European Application No. 16847351, European Search Report and Opinion, mailed Jan. 4, 2019.
Flotte et al., Gene expression from adeno-associated virus vectors in airway epithelial cells, Am. J. Respir. Mol. Biol., 7:349-56 (1992).
Forbes et al., Skeletal muscles of ambulant children with Duchenne muscular dystrophy: validation of multicenter study of evaluation with MR imaging and MR spectroscopy, Radiology, 269:198-207 (2013).
Gao et al., Glades of adeno-associated viruses are widely disseminated in human tissues, J. Virol., 78:6381-6388 (2004).
GenBank Accession No. AF085716, Adeno-associated virus 5 DNA binding trs helicase (Rep22) and capsid protein (VP1) aenes, complete eds, Feb. 9, 1999.
GenBank Accession No. AX753246, Sequence 1 from Patent EP1310571, Jun. 23, 2003.
GenBank Accession No. AX753249, Sequence 4 from Patent EP1310571, Jun. 23, 2018.
GenBank Accession No. M21390.1, Online Available at https://www.ncbi.nlm.nih.gov/nucleotide/A121390.I?report=genbank&log$=nucltop&blast rank=3 & RID=0G3UPTM4013#sequence ?21390.1.
GenBank Accession No. NC_001401, Adeno-associated virus—2, complete genome, Aug. 13, 2018.
GenBank Accession No. NC_001729, Adeno-associated virus—3, complete genome, Aug. 13, 2018.
GenBank Accession No. NC_001829, Adeno-associated virus—4, complete genome, Aug. 13, 2018.
GenBank Accession No. NC_002077, Adeno-associated virus—1, complete genome, Aug. 13, 2018.
GenBank Assession No. AF028704, Adeno-associated virus 6, complete genome, Jan. 12, 1998.
Govoni et al., Ongoing therapeutics trials and outcome measures for Duchenne muscular dystrophy, Cell Mol. Life Sci., 70:4585-602 (2013).
Hermonat et al., Use of adeno-associated virus as a mammalian DNA cloning vector: transduction of neomycin resistance into mammalian tissue culture cells, Proc. Natl. Acad. Sci. USA., 81:6466-70 (1984).
Howard MK, GeneSeq Accession No. AAF30284, computer printout, 7-8 (2001).
International Application No. PCT/US16/52051, International Search Report and Written Opinion, mailed Dec. 30, 2016.
International Preliminary Report on Patentability, PCT/US2016/052051, dated Mar. 20, 2018.
Johnson et al., Muscle creatine kinase sequence elements regulating skeletal and cardiac muscle expression in transgenic mice, Mol. Cell Biol., 9:3393-9 (1989).
Laughlin et al., Cloning of infectious adeno-associated virus genomes in bacterial plasmids, Gene., 23:65-73 (1983).
Lebkowski et al., Adena-associated virus: a vector system for efficient introduction and integration of DNA into a variety of mammalian cell types, Mol. Cell. Biol., 7:349 (1988).
Mader et al., A steroid-inducible promoter for the controlled overexpression of cloned genes in eukaryotic cells, Proc. Natl. Acad. Sci. USA., 90:5603-7 (1993).
Marshall et al., Sarcospan-dependent Akt activation is required for utrophin expression and muscle regeneration, J. Cell Biol., 197:1009-1027 (2012).
Marsic et al., Vector design Tour de Force: integrating combinatorial and rational approaches to derive novel adeno-associated virus variants, Mol. Ther., 22:1900-1909 (2014).
Martin et al., Overexpression of Galgt2 in skeletal muscle prevents injury resulting from eccentric contractions in both mdx and wild-type mice, AJP Cell Phys., 296(3):C476-C488 (2008).
Martin, Glycobiology of the neuromuscular junction, J. Neurocytol., 32:915-29 (2003).
Martin, Translational Studies of GALGT2 Gene Therapy for Duchenne Muscular Dystrophy, AWARD No. W81XWH-12-1-0416; US Army Medical Research and Materiel Command, Report Date Oct. 2013.
Mateos-Aierdi, et al., Advances in gene therapies for limb-girdle muscular dystrophies, Sep. 2014 (Abstract Only).
McLaughlin et al., Adena-associated virus general transduction vectors, analysis of proviral structures, J. Virol., 62:1963-73 (1988).
Molecular Therapy Information for Authors, Feb. 1, 2019.
Montiel et al., Geneseq Accession No. AJ517771, computer printout, 11-14, direct submission, 11-14 (2002).
Mori et al., Two novel adeno-associated viruses from cynomolgus monkey: pseudotyping characterization of capsid protein, Virology, 330:375-83 (2004).
Muscat at al., Multiple 5'-flanking regions of the human alpha-skeletal actin gene synergistically modulate muscle-specific expression, Mol. Cell Biol., 7:4089-99 (1987).
Muzyczka, Use of adeno-associated virus as a general transduction vector for mammalian cells, Curr. Top. Microbiol. Immunol., 158:97-129 (1992).
Nguyen et al., Overexpression of the cytotoxic T cell GaINAc transferase in skeletal muscle inhibits muscular dystrophy in mdx mice, Proc. Natl. Acad. Sci. USA., 99:5616-5621 (2002).
Paul et al., Increased viral titer through concentration of viral harvests from retroviral packaging lines, Hum. Gene Ther., 4:609-15 (1993).
Perrin et al., An experimental rabies vaccine produced with a new BHK-21 suspension cell culture process: use of serum-free medium and perfusion-reactor system, Vaccine, 13:1244-50 (1995).
Rabinowitz et al., Cross-packaging of a single adeno-associated virus AAC_ type 2 vector genome into multiple AAV serotypes enables transduction with broad specificity, J. Virol., 76:791-801 (2002).

(56) References Cited

OTHER PUBLICATIONS

Rodino-Klapac et al., Micro-dystrophin and follistatin co-delivery restore muscle function in aged DMD model, Human Molec. Gen., 22(24):4929-4937 (2013).
Rodino-Klapac et al., Persistent expression of FLAG-tagged micro dystrophin in nonhuman primates following intramuscular and vascular delivery, Mol. Ther., 18:109-17 (2010).
Salva et al., Design of tissue-specific regulatory cassettes for high-level rAAV-mediated expression in skeletal and cardiac muscle, Mol. Ther., 15:320-9 (2007).
Samulski et al. Cloning of adeno-associated virus into pBR322: rescue of intact virus from the recombinant plasmid in human cells, Proc. Natl. Acad. Sci. USA., 79:2077-81 (1982).
Samulski et al., Helper-free stocks of recombinant adeno-associated viruses: normal integration does not require viral gene expression, J. Virol., 63:3822-8 (1989).
Samulski, GeneSeq Accession No. AOG17648, computer printout, 15-16 (2007).
Schnepp et al., Highly purified recombinant adeno-associated virus vectors. Preparation and quantitation, Methods Mol. Med., 69:427-43 (2002).
Semenza et al., Hypoxia-inducible nuclear factors bind to an enhancer element located 3' to the human erythropoietin gene, Proc. Natl. Acad. Sci. USA., 88:5680-4 (1991).
Senapathy et al. Molecular cloning of adeno-associated virus variant genomes and generation of infectious virus by recombinant in mammalian cells, J. Biol. Chem., 259:4661-6 (1984).
Srivastava et al., Nucleotide sequence and organization of the adeno-associated virus 2 genome, J. Virol., 45:555-64 (1983).
Sternberg et al., Identification of Upstream and Intragenic Regulatory Elements That Confer Cell-Type-Restricted and Differentiation-Specific Expression on the Muscle Creatine Kinase Gene, Mol. Cell. Bio., 8(7):2896-2909 (1988).
Thomas et al., B4GALNT2 (GALGT2) Gene therapy reduces skeletal muscle pathology in the fkrp p448I mouse model of limb girdle muscular dystrophy 21, Am. J. Pathol., 186(9):2429-2448 (2016).
Tratschin et al., A human parvovirus, adeno-associated virus, as a eucaryotic vector: transient expression and encapsidation of the procaryotic gene for chloramphenicol acetyltransferase, Mol. Cell Biol., 4:2072-2081 (1984).
Tratschin et al., Adena-associated virus vector for high-frequency integration, expression, and rescue of aenes in mammalian cells, Mol. Cell Biol., 5:3251-60 (1985).
Wang et al., Recombinant AAV serotype 1 transduction efficiency and tropism in the murine brain, Gene. Ther., 10:1528-34 (2003).
Weintraub et al., The myoD gene family: nodal point during specification of the muscle cell lineage, Science, 251:761-6 (1991).
White et al., GeneSeq Accession No. AEF99304, computer printout, 3-4 (2006).
Xu et al., Deletion of Galgt2 (B4Galnt2) Reduces Muscle Growth in Response to Acute Injury and Increases Muscle Inflammation and Pathology in Dystrophin-Deficient Mice, American Journal of Pathology, 185:2668-2684 (2015).
Xu et al., Overexpression of GALGT2 in Skeletal Muscles Via AAV Prevents Muscle Damage and Inhibits Muscle Pathology in Mouse Models of Muscular Dystrophy, Molecular Thererapy, S201 (2009).
Xu et al., Overexpression of Galgt2 reduces dystrophic pathology in the skeletal muscles of alpha sarcoglycan-deficient mice, Am. J. Pathol., 175:235-47 (2009).
Xu et al., Overexpression of the cytotoxic T cell (CT) carbohydrate inhibits muscular dystrophy in the dyW mouse model of congenital muscular dystrophy 1A, Am. J. Pathol., 171:181-99 (2007).
Xu et al., Postnatal overexpression of the CT GaINAc transferase inhibits muscular dystrophy in mdx mice without altering muscle growth or meuromuscula development: evidence for a utrophin-independent mechanism, Neuromuscul. Disord., 17:209-20 (2007).
You, GeneSeq Accession No. ARZ08701, computer printout, 10-11 (2008).
Yuasa et al., Adeno-associated virus vector-mediated gene transfer into dystrophin-deficient skeletal muscle evokes enhanced immune response against the transgene product, Gen Ther., 9:1576-1588 (2002).
Ozawa, Gene therapy using AAV, Uirusu, 57: 47-56, (Jun. 2007).
Genbank Accession No. AJ517771.1, Homo sapiens partial mRNA for sda beta-1,4-GaINAc transferase (GALGT2 gene), splice variant 2, Nov. 20, 2002.
Genbank Accession No. AF188002.1, Mus musculus muscle creatine kinase (Mck) gene, promoter region, Sep. 15, 2000.

\* cited by examiner

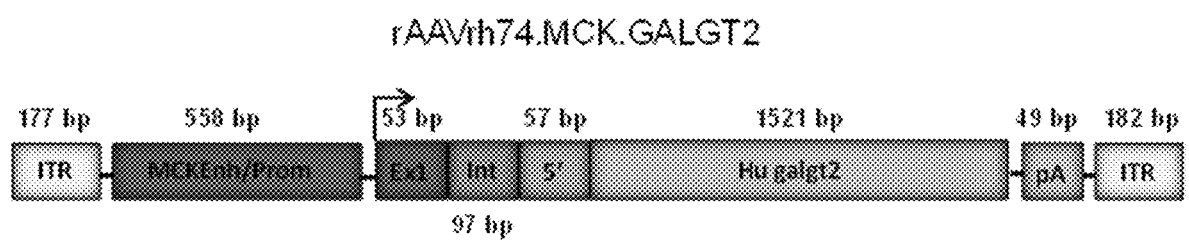

METHODS AND MATERIALS FOR GALGT2 GENE THERAPY

METHODS AND MATERIALS FOR GALGT2 GENE THERAPY

This application is a continuation of U.S. patent application Ser. No. 15/759,474, filed Mar. 12, 2018, which is a national phase application of PCT Application No. PCT/US16/52051, filed Sep. 16, 2016, which claims priority benefit of U.S. Provisional Application No. 62/301,260, filed Feb. 29, 2016, U.S. Provisional Application No. 62/221,068, filed on Sep. 20, 2015 and U.S. Provisional Application No. 62/220,107, filed Sep. 17, 2015, all of which are incorporated by reference herein in their entirety.

STATEMENT OF GOVERNMENT INTEREST

This invention was made with government support under U54 NS055958 and R01 AR049722 awarded by the National Institutes of Health. The government has certain rights in the invention.

INCORPORATION BY REFERENCE OF THE SEQUENCE LISTING

This application contains, as a separate part of disclosure, a Sequence Listing in computer-readable form (filename: 49985A_Seqlisting.txt; 14,552 bytes—ASCII text file; created Mar. 16, 2021) which is incorporated by reference herein in its entirety.

FIELD

The present disclosure relates to recombinant adeno-associated virus (rAAV) delivery of a GALGT2 polynucleotide. The disclosure provides rAAV and methods of using the rAAV for GALGT2 gene therapy of neuromuscular disorders. Exemplary neuromuscular disorders include, but are not limited, to muscular dystrophies such as Duchenne muscular dystrophy, Congenital Muscular Dystrophy 1A and Limb Girdle Muscular Dystrophy 2D.

BACKGROUND

Muscular dystrophies (MDs) are a group of genetic diseases. The group is characterized by progressive weakness and degeneration of the skeletal muscles that control movement. Some forms of MD develop in infancy or childhood, while others may not appear until middle age or later. The disorders differ in terms of the distribution and extent of muscle weakness (some forms of MD also affect cardiac muscle), the age of onset, the rate of progression, and the pattern of inheritance.

One type of MD is Duchenne muscular dystrophy (DMD). It is the most common severe childhood form of muscular dystrophy affecting 1 in 5000 newborn males. Inheritance follows an X-linked recessive pattern. DMD is caused by mutations in the DMD gene leading to absence of dystrophin protein (427 KDa) in skeletal and cardiac muscles, as well as GI tract and retina. Dystrophin not only protects the sarcolemma from eccentric contractions, but also anchors a number of signaling proteins in close proximity to sarcolemma. Clinical symptoms of DMD are usually first noted between ages 3 to 5 years, with altered gait and reduced motor skills typically leading to diagnostic evaluation. DMD is relentlessly progressive, with loss of ambulation by age twelve. Historically patients died from respiratory complications late in the second decade, but improved supportive care—and in particular judicious use of nocturnal ventilatory support—has extended life expectancy by nearly a decade. Prolonging life unmasks the nearly universal decline in cardiac function, with complications of dilated cardiomyopathy. This poses further clinical challenges and a need for recognition and medical intervention that did not previously exist. Non-progressive cognitive dysfunction may also be present in DMD. Despite virtually hundreds of clinical trials in DMD, treatment with corticosteroids remains the only treatment that has consistently demonstrated efficacy. Current standard of care for DMD involves use of prednisone or deflazacort, which can prolong ambulation by several years at the expense of significant side effects, and has limited evidence for any impact on survival.

Another type of MD is Congenital Muscular Dystrophy 1A (MCD1A). MCD1A belongs to a group of neuromuscular disorders with onset at birth or infancy characterized by hypotonia, muscle weakness and muscle wasting. MCD1A represents 30-40% of congenital muscular dystrophies, with some regional variation. Prevalence is estimated at 1/30,000. The disease presents at birth or in the first few months of life with hypotonia and muscle weakness in the limbs and trunk. Respiratory and feeding disorders can also occur. Motor development is delayed and limited (sitting or standing is only possible with help). Infants present with early rigidity of the vertebral column, scoliosis, and respiratory insufficiency. There is facial involvement with a typical elongated myopathic face and ocular ophthalmoplegia disorders can appear later. Epileptic attacks are possible, although they occur in less than a third of subjects. Intellectual development is normal. MCD1A is caused by mutations in the LAMA2 gene coding for the alpha-2 laminin chain. Transmission is autosomal recessive. Current treatment is symptomatic. It consists of a multidisciplinary approach, including physiotherapists, occupational therapists and speech-language therapists, with the objective of optimizing each subject's abilities. Seizures or other neurological complications require specific treatment. The prognosis of MDC1A is very severe as a large proportion of affected children do not reach adolescence. Currently, the prognosis can only be improved by attentive multidisciplinary (particularly orthopedic and respiratory) management.

Yet another type of MD is Limb Girdle Muscular Dystrophy (LGMD). LGMDs are rare conditions and they present differently in different people with respect to age of onset, areas of muscle weakness, heart and respiratory involvement, rate of progression and severity. LGMDs can begin in childhood, adolescence, young adulthood or even later. Both genders are affected equally. LGMDs cause weakness in the shoulder and pelvic girdle, with nearby muscles in the upper legs and arms sometimes also weakening with time. Weakness of the legs often appears before that of the arms. Facial muscles are usually unaffected. As the condition progresses, people can have problems with walking and may need to use a wheelchair over time. The involvement of shoulder and arm muscles can lead to difficulty in raising arms over head and in lifting objects. In some types of LGMD, the heart and breathing muscles may be involved.

There are at least nineteen forms of LGMD, and the forms are classified by their associated genetic defects.

| Type | Pattern of Inheritance | Gene or Chromosome |
| --- | --- | --- |
| LGMD1A | Autosomal dominant | Myotilin gene |
| LGMD1B | Autosomal dominant | Lamin A/C gene |
| LGMD1C | Autosomal dominant | Caveolin gene |
| LGMD1D | Autosomal dominant | Chromosome 7 |
| LGMDIE | Autosomal dominant | Desmin gene |
| LGMD1F | Autosomal dominant | Chromosome 7 |
| LGMD1G | Autosomal dominant | Chromosome 4 |
| LGMD1H | Autosomal dominant | Chromosome 3 |
| LGMD2A | Autosomal recessive | Calpain-3 gene |
| LGMD2B | Autosomal recessive | Dysferlin gene |
| LGMD2C | Autosomal recessive | Gamma-sarcoglycan gene |
| LGMD2D | Autosomal recessive | Alpha-sarcoglycan gene |
| LGMD2E | Autosomal recessive | Beta-sarcoglycan gene |
| LGMD2F | Autosomal recessive | Delta-sarcoglycan gene |
| LGMD2G | Autosomal recessive | Telethonin gene |
| LGMD2H | Autosomal recessive | TRIM32 |
| LGMD2I | Autosomal recessive | FKRP gene |
| LGMD2J | Autosomal recessive | Titin gene |
| LGMD2K | Autosomal recessive | POMTI gene |
| LGMD2L | Autosomal recessive | Fukutin gene |
| LGMD2M | Autosomal recessive | Fukutin gene |
| LGMD2N | Autosomal recessive | POMT2 gene |
| LGMD2O | Autosomal recessive | POMGnT1 gene |
| LGMD2Q | Autosomal recessive | Plectin gene |

Specialized tests for LGMD are now available through a national scheme for diagnosis, the National Commissioning Group (NCG).

The GALGT2 gene (otherwise known as B4GALNT2) encodes a ß1-4-N-acetyl-D-galactosamine (βGalNAc) glycosyltransferase. GALGT2 overexpression has been studied in three different models of muscular dystrophy: DMD, LGMD2D and MDC1A [Xu et al., *Am. J. Pathol*, 175: 235-247 (2009); Xu et al., *Am. J. Path.*, 171: 181-199 (2007); Xu et al., *Neuromuscul. Disord.*, 17: 209-220 (2007); Martin et al., *Am. J. Physiol. Cell. Physiol.*, 296: C476-488 (2009); and Nguyen et al., *Proc. Natl. Acad. Sci. USA*, 99: 5616-5621 (2002)]. GALGT2 overexpression in skeletal muscles has been reported to induce the glycosylation of alpha dystroglycan with β1-4-N-acetyl-D-galactosamine (GalNAc) carbohydrate to make the CT carbohydrate antigen (Neu5Ac/Gcα2-3[GalNAcβ1-4]Galβα1-4GlcNAcβ-). The GALGT2 glycosyltransferase and the CT carbohydrate it creates are normally confined to neuromuscular and myotendinous junctions in skeletal muscles of adult humans, non-human primates, rodents and all other mammals yet studied [Martin et al., *J. Neurocytol.*, 32: 915-929 (2003)]. Overexpression of GALGT2 in skeletal muscle has been reported to stimulate the ectopic glycosylation of the extrasynaptic membrane, stimulating the ectopic overexpression of a scaffold of normally synaptic proteins that are orthologues or homologues of proteins missing in various forms of muscular dystrophy, including dystrophin surrogates (e.g., utrophin, Plectin1) and laminin α2 surrogates (laminin α5 and agrin) [Xu et al. 2009, supra; Xu et al, *Am. J. Path.* 2007, supra; Xu et al., *Neuromuscul. Disord.* 2007, supra; Nguyen et al., supra; Chicoine et al., *Mol. Ther*, 22: 713-724. (2014). As a group, the induction of such surrogates by GALGT2 has been reported to strengthen sarcolemmal membrane integrity and prevent muscle injury in dystrophin-deficient muscles as well as in wild type muscles [Martin et al., supra]. GALGT2 overexpression in skeletal muscle has been reported to prevent muscle damage and inhibit muscle disease. This is true in the mdx mouse model for DMD [Xu et al., *Neuromuscul. Disord.* 2007, supra; Martin et al. (2009), supra; Nguyen et al., supra], where improvement equal to that of micro-dystrophin gene transfer is noted even though only half the number of fibers were transduced [Martin et al. (2009), supra]. Notably, GALGT2 gene transfer has also been reported to be preventive in the $dy^W$ model for congenital muscular dystrophy 1A [Xu et al, *Am. J. Path.* 2007, supra] and the Sgca$^{-/-}$ mouse model for limb girdle muscular dystrophy type 2D [Xu et al. 2009, supra].

Adeno-associated virus (AAV) is a replication-deficient parvovirus, the single-stranded DNA genome of which is about 4.7 kb in length including 145 nucleotide inverted terminal repeat (ITRs). There are multiple serotypes of AAV. The nucleotide sequences of the genomes of the AAV serotypes are known. For example, the complete genome of AAV-1 is provided in GenBank Accession No. NC_002077; the complete genome of AAV-2 is provided in GenBank Accession No. NC 001401 and Srivastava et al., *J. Virol.*, 45: 555-564 {1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., *J. Virol.*, 78: 6381-6388 (2004); the AAV-10 genome is provided in *Mol. Ther.*, 13(1): 67-76 (2006); and the AAV-11 genome is provided in *Virology*, 330(2): 375-383 (2004). Cis-acting sequences directing viral DNA replication (rep), encapsidation/packaging and host cell chromosome integration are contained within the AAV ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA. The rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

An AAV termed rh.74 has been used to deliver DNAs encoding various proteins. Xu et al., *Neuromuscular Disorders*, 17: 209-220 (2007) and Martin et al., *Am. J. Physiol. Cell. Physiol.*, 296: 476-488 (2009) relate to rh. 74 expression of cytotoxic T cell GalNAc transferase for Duchenne muscular dystrophy. Rodino-Klapac et al., *Mol. Ther.*, 18(1): 109-117 (2010) describes AAV rh.74 expression of a microdystrophin FLAG protein tag fusion after delivery of the AAV rh. 74 by vascular limb perfusion.

The muscular dystrophies are a group of diseases without identifiable treatment that gravely impact individuals, families, and communities. The costs are incalculable. Individuals suffer emotional strain and reduced quality of life associated with loss of self-esteem. Extreme physical challenges resulting from loss of limb function creates hardships in activities of daily living. Family dynamics suffer through financial loss and challenges to interpersonal relationships. Siblings of the affected feel estranged, and strife between spouses often leads to divorce, especially if responsibility for the muscular dystrophy can be laid at the feet of one of the parental partners. The burden of quest to find a cure often becomes a life-long, highly focused effort that detracts and challenges every aspect of life. Beyond the family, the community bears a financial burden through the need for added facilities to accommodate the handicaps of the muscular dystrophy population in special education, special transportation, and costs for recurrent hospitalizations to treat recurrent respiratory tract infections and cardiac complications. Financial responsibilities are shared by state and federal governmental agencies extending the responsibilities to the taxpaying community.

There thus remains a significant need in the art for treatments for neuromuscular disorders including, but not limited to, muscular dystrophies such as DMD, MDC1A and LGMD2D.

SUMMARY

Provided herein are methods of treating a neuromuscular disorder in a subject in need thereof in which a recombinant adeno-associated virus (rAAV) such as rAAVrh74.MCK.GALGT2 is administered to the subject, where: the route of administration is an intramuscular route and the dose of the rAAV administered is about $3\times10^{11}$ vg/injection to about $5\times10^{12}$ vg/injection, the route of administration is an intramuscular route and the dose of the rAAV administered is about $3\times10^{11}$ vg/injection, the route of administration is an intramuscular route and the dose of the rAAV administered is about $1\times10^{12}$ vg/injection, the route of administration is an intramuscular route and the dose of the rAAV administered is about $5\times10^{12}$ vg/injection, the route of administration is inter-arterial limb perfusion and the dose of the rAAV administered is about $6\times10^{12}$ vg/kg/limb to about $4.8\times10^{13}$ vg/kg/limb, the route of administration is inter-arterial limb perfusion and the dose of the rAAV administered is about $6\times10^{12}$ vg/kg/limb, the route of administration is inter-arterial limb perfusion and the dose of the rAAV administered is about $1.2\times10^{13}$ vg/kg/limb, the route of administration is inter-arterial limb perfusion and the dose of the rAAV administered is about $2.4\times10^{13}$ vg/kg/limb, the route of administration is inter-arterial limb perfusion and the dose of the rAAV administered is about $4.8\times10^{13}$ vg/kg/limb, the route of administration is systemic intravenous administration and the dose of the rAAV administered is about $2\times10^{14}$ vg/kg to about $6\times10^{15}$ vg/kg, the route of administration is systemic intravenous administration and the dose of the rAAV administered is about $4\times10^{14}$ vg/kg to about $6\times10^{15}$ vg/kg, the route of administration is systemic intravenous administration and the dose of the rAAV administered is about $4\times10^{14}$ vg/kg, the route of administration is systemic intravenous administration and the dose of the rAAV administered is about $8\times10^{14}$ vg/kg, the route of administration is systemic intravenous administration and the dose of the rAAV administered is about $2\times10^{15}$ vg/kg or the route of administration is systemic intravenous administration and the dose of the rAAV administered is about $6\times10^{15}$ vg/kg.

Examples of neuromuscular disorder for which treatment is contemplated are Duchenne Muscular Dystrophy (DMD); Becker Muscular Dystrophy; Congenital Muscular Dystrophy (MDC) 1A, 1B, 1C and 1D; Limb Girdle Muscular Dystrophy (LGMD) 1A, 1B, 1C, 1D, 1E, 1F, 1G, 1H, 2A, 2B, 2C, 2D, 2E, 2F, 2G 2H, 2I, 2J, 2K, 2L, 2M, 2N, 2O and 2Q; Bethlem Myopathy; Ullrich Congenital Muscular Dystrophy; Muscle Eye Brain Disease; Fukuyama Congenital Muscular Dystrophy; Walker Warburg Syndrome; Myotonic Dystrophy; Myasthenic syndromes; Congenital Myasthenias; Inclusion Body Myopathy; Inclusion Body Myositis; Emery Dreifuss Muscular Dystrophy; Distal Muscular Dystrophy; Dermatomyositis; Centronuclear Myopathy; Faciosacpulohumeral Muscular Dystrophy; Myoshi Myopathy; Mitochondrial Myopathy; Nemaline Myopathy; Nonaka Myopathy; Myasthenia Gravis; and Polymyositis. Thus, among others, muscular dystrophies are neuromuscular disorders contemplated.

The methods result in an improvement in the human subject, for example, in absolute muscle specific force; force decrement during eccentric muscle contractions; serum CK level; serum cardiac troponin level; serum MMP9 level; grip strength; limb torque; limb mobility or flexibility; ambulation; 6 minute walk test; knee flexor or extensor strength; maximal voluntary isometric muscle contraction; North Star Ambulatory Assessment; muscle mass, fat reduction, or edema by limb T2-weighted MRI measures; muscle contractures; limb joint angle; heart function (heart rate, cardiac output, percent fractional shortening, stroke volume); respiration (including respiratory rate, blood oxygenation, need for supplemental oxygen); muscle necrosis; muscle regeneration; muscle wasting; muscle inflammation; muscle calcification; muscle central nucleation; muscle size or myofiber size; lifespan; and/or dystrophin or laminin alpha 2 surrogate protein expression (utrophin, plectin 1, laminin alpha 5, agrin).

Also provided herein are rAAV encoding a GALGT2 polypeptide such as the rAAVrh74.MCK.GALGT2.

DETAILED DESCRIPTION

The present disclosure provides methods and products for treating neuromuscular disorders. The methods involve delivery of GALGT2 polynucleotides to muscle cells in a subject using AAV as a gene delivery vector. Subjects include, but are not limited to, mammals such as dogs, cats and humans. In some embodiments, the subjects are human patients. In some embodiments, the subjects are human pediatric patients.

In one aspect, methods are provided for the treatment of neuromuscular disorders comprising administering to a subject a recombinant AAV (rAAV) encoding GALGT2.

Neuromuscular disorders contemplated herein include, but are not limited to, a muscular dystrophy (MD). Neuromuscular disorders contemplated herein, also include neuromuscular disorders other than MDs. Thus, in some embodiments, neuromuscular disorders contemplated herein include, but are not limited to, Duchenne Muscular Dystrophy (DMD); Becker Muscular Dystrophy; Congenital Muscular Dystrophy (MDC) 1A, 1B, 1C and 1D; Limb Girdle Muscular Dystrophy (LGMD) 1A, 1B, 1C, 1D, 1E, 1F, 1G, 1H, 2A, 2B, 2C, 2D, 2E, 2F, 2G 2H, 2I, 2J, 2K, 2L, 2M, 2N, 2O and 2Q; Bethlem Myopathy; Ullrich Congenital Muscular Dystrophy; Muscle Eye Brain Disease; Fukuyama Congenital Muscular Dystrophy; Walker Warburg Syndrome; Myotonic Dystrophy; Myasthenic syndromes; Congenital Myasthenias; Inclusion Body Myopathy; Inclusion Body Myositis; Emery Dreifuss Muscular Dystrophy; Distal Muscular Dystrophy; Dermatomyositis; Centronuclear Myopathy; Faciosacpulohumeral Muscular Dystrophy; Myoshi Myopathy; Mitochondrial Myopathy; Nemaline Myopathy; Nonaka Myopathy; Myasthenia Gravis; and Polymyositis. In some embodiments, the MD is DMD. In some embodiments, the MD is MDC1A. In some embodiments, the MD is LGMD2D.

In some embodiments of any of the methods described herein, the subject is at least 1 year of age (e.g., at least 1, 2, 3, 4, 5, 6, 7, 8, 9, 10, 11, 12, 13, 14, 15, 16, 17, 18, 19, or 20) or older. In some embodiments of any of the methods described herein, the subject is a male. In some embodiments of any of the methods described herein, the subject is a female. In some embodiments of any of the methods described herein, the subject is ambulant at the time of treatment. In some embodiments of any of the methods described herein, the subject is non-ambulant at the time that treatment begins. In some embodiments of any of the methods described herein, the subject is one having a confirmed mutation in the DMD gene using a clinically accepted technique that defines the mutation. Mutations in the dystrophin gene that give rise to a DMD phenotype are well known in the art, as are methods for identifying them in a subject. See, e.g., the Leiden Duchenne muscular dystrophy mutation database, Leiden University Medical Center, The Netherlands, and Aartsma-Rus et al., *Hum. Mut.*, 30:293-299 (2009).

In some embodiments of any of the methods described herein, the subject, by magnetic resonance imaging of the extensor digitorum *brevis* (EDB) muscle, exhibits a preservation of sufficient muscle mass to permit transfection or gene transfer. In some embodiments of any of the methods described herein, the subject is receiving a stable dose of corticosteroid therapy (e.g., deflazacort, prednisone, or a generic form thereof), e.g., for at least 4 (e.g., 5, 6, 7, 8, 9, 10, 11, or 12) weeks prior to beginning treatment. In certain embodiments, the subject is on background steroid therapy (e.g., intermittent or chronic/continuous background steroid therapy). One of skill in the art would appreciate that such subjects are those who are subject to ongoing use of steroids (or corticosteroids) on top of which another treatment, such as the gene therapy described herein, is administered.

In some embodiments of any of the methods described herein, the subject is one that does not have an active viral infection. In some embodiments of any of the methods described herein, the subject the subject does not have a DMD mutation in the absence of weakness or loss of function. In some embodiments of any of the methods described herein, the subject does not exhibit symptoms of cardiomyopathy, such as dyspnea on exertion, pedal edema, shortness of breath upon lying flat, or rales at the base of the lung. In some embodiments of any of the methods described herein, the subject does not, by echocardiogram, have an ejection fraction below about 40%. In some embodiments of any of the methods described herein, the subject is not one for whom serological evidence exists at the time of treatment of infection with HIV (since the subject may be in an immunocompromised state) or Hepatitis A, B, or C (since the subject may have transaminase elevation).

In some embodiments of any of the methods described herein, the subject has not been diagnosed, does not have, or is not being treated for an autoimmune disease. In some embodiments of any of the methods described herein, the subject does not have persistent leukopenia or leukocytosis (white blood cell count ≤3.5 K/µL or ≥20.0 K/µL) or an absolute neutrophil count <1.5 K/µL.

In some embodiments of any of the methods described herein, the subject does not have a concomitant illness (e.g., viral infection or autoimmune disease) or requirement for chronic drug treatment that in the opinion of a medical practitioner creates an unnecessary risk for gene transfer.

In some embodiments of any of the methods described herein, the subject does not have an rAAVrh74 binding antibody titer of ≤1:400 as determined by an ELISA immunoassay. In some embodiments of any of the methods described herein, the subject does not have an rAAVrh74 binding antibody titer of ≤1:50 as determined by an ELISA immunoassay.

In some embodiments of any of the methods described herein, the subject does not have detectable circulating anti-Sda antibodies, e.g., as determined by ELISA immunoassay of a biological sample of the subject [Blood groups: P, I, Sda, and Pr. AABB (1991)]. The Sda glycan is the human blood group structure made by GALGT2. The Sda blood group antigen is identical to the CT glycan structure made by GALGT2 in mice [GalNAcb1,4[Neu5Aca2,3] Galb1,4GlcNAc-]. While the disclosure is not bound by any particular theory or mechanism of action, the presence or amount of the CT glycan structure is expected to be enhanced on cells expressing GALGT2 and the inventors believe that subjects with such Sda antibodies, estimated to be 0.2% of the subject population, may be at risk of antibody-mediated tissue rejection after rAAVrh74.MCK.GALGT2 treatment.

Suitable biological samples for use in the methods described herein include, e.g., any biological fluid. A biological sample can be, for example, a specimen obtained from a subject (e.g., a mammal such as a human) or can be derived from such a subject. A biological sample can be from a muscle biopsy. A biological sample can also be a biological fluid such as urine, whole blood or a fraction thereof (e.g., plasma or serum), saliva, semen, sputum, cerebrospinal fluid, tears, or mucus. A biological sample can be further fractionated, if desired, to a fraction containing particular analytes (e.g., proteins) of interest. For example, a whole blood sample can be fractionated into serum or into fractions containing particular types of proteins. If desired, a biological sample can be a combination of different biological samples from a subject such as a combination of two different fluids.

Biological samples suitable for the invention may be fresh or frozen samples collected from a subject, or archival samples with known diagnosis, treatment and/or outcome history. The biological samples can be obtained from a subject, e.g., a subject having, suspected of having, or at risk of developing, a cancer or an infection (e.g., a viral infection). Any suitable methods for obtaining the biological samples can be employed, although exemplary methods include, for example, open muscle biopsy, phlebotomy, swab (e.g., buccal swab), lavage, or fine needle aspirate biopsy procedure. Biological samples can also be obtained from bone marrow or spleen.

In some embodiments, a protein extract may be prepared from a biological sample. In some embodiments, a protein extract contains the total protein content. Methods of protein extraction are well known in the art. See, for example, Roe "Protein Purification Techniques: A Practical Approach", 2nd Edition, Oxford University Press (2001). Numerous different and versatile kits can be used to extract proteins from bodily fluids and tissues, and are commercially-available from, for example, BioRad Laboratories (Hercules, CA), BD Biosciences Clontech (Mountain View, CA), Chemicon International, Inc. (Temecula, CA), Calbiochem (San Diego, CA), Pierce Biotechnology (Rockford, IL), and Invitrogen Corp. (Carlsbad, CA).

Methods for obtaining and/or storing samples that preserve the activity or integrity of cells in the biological sample are well known to those skilled in the art. For example, a biological sample can be further contacted with one or more additional agents such as appropriate buffers and/or inhibitors, including protease inhibitors, the agents meant to preserve or minimize changes (e.g., changes in osmolarity or pH) in protein structure. Such inhibitors include, for example, chelators such as ethylenediamine tetraacetic acid (EDTA), ethylene glycol tetraacetic acid (EGTA), protease inhibitors such as phenylmethylsulfonyl fluoride (PMSF), aprotinin, and leupeptin. Appropriate buffers and conditions for storing or otherwise manipulating whole cells are described in, for example, Pollard and Walker, "Basic Cell Culture Protocols," Volume 75 of Methods in Molecular Biology, Humana Press (1997); Masters, "Animal cell culture: a practical approach," Volume 232 of Practical Approach Series, Oxford University Press (2000); and Jones "Human cell culture protocols," Volume 2 of Methods in Molecular Medicine, Humana Press (1996).

The methods of treating neuromuscular disorders disclosed herein result in transduction of muscle cells (e.g., skeletal muscle, smooth muscle or cardiac muscle cells) with GALGT2 polynucleotide. An effective dose, or effective multiple doses, of a composition comprising a rAAV of the disclosure to a subject is a dose that prevents, slows progression of, or ameliorates (eliminates or reduces) muscle pathology associated with the neuromuscular disorder being treated. An effect on muscle pathology can be demonstrated by an improvement in one or more measures standard in the art such as: absolute muscle specific force; force decrement during eccentric muscle contractions; serum CK level; serum cardiac troponin level; serum MMP9 level; grip strength; limb torque; limb mobility or flexibility; ambulation; 6 minute walk test; knee flexor or extensor strength; maximal voluntary isometric muscle contraction; North Star Ambulatory Assessment; muscle mass, fat reduction, or edema by limb T2-weighted MRI measures; muscle contractures; limb joint angle; heart function (heart rate, cardiac output, percent fractional shortening, stroke volume); respiration (including respiratory rate, blood oxygenation, need for supplemental oxygen); muscle necrosis; muscle regeneration; muscle wasting; muscle inflammation; muscle calcification; muscle central nucleation; muscle size or myofiber size; lifespan; and dystrophin or laminin alpha 2 surrogate protein expression (utrophin, plectin 1, laminin alpha 5, agrin). See, for example, Forbes et al., *Radiology*, 269(1): 198-207 (2013); Govoni et al., *Cell Mol. Life Sci.*, 70(23): 4585-4602 (2013); and Chandrasekharan and Martin, *Methods Enzymol.*, 479: 291-322 (2010). If a dose is administered prior to development of a neuromuscular disorder, the administration is prophylactic. If a dose is administered after the development of a neuromuscular disorder, the administration is therapeutic. The treatment of the subject by methods described herein is therefore contemplated to prevent, slow or prevent progression of, diminish the extent of, result in remission (partial or total) of, and/or prolong survival of a neuromuscular disorder.

In some embodiments, any of the methods described herein can further comprise detecting or measuring the level of expression of GALGT2 in cells transduced with the GALGT2 transgene. Methods for measuring mRNA or protein expression are well known in the art (e.g., immunoassays, such as Western blotting).

In some embodiments, any of the methods described herein can further comprise detecting or measuring the amount of CT antigen expressed on cells transduced with the GALGT2 polynucleotide [Chicoine et al., supra].

In some embodiments, any of the methods described herein can further comprise detecting or measuring the amount of utrophin expressed on cells transduced with the GALGT2 polynucleotide [Chicoine et al., supra].

In some embodiments, any of the methods described herein can further comprise detecting or measuring the number of fibers containing central nuclei, which fibers were transduced with the GALGT2 polynucleotide.

Routes of administration for the rAAV contemplated in the foregoing methods therefore include, but are not limited to, intraperitoneal (IP), intramuscular (IM) and intravascular [including, for example, inter-arterial limb perfusion (ILP) and intravenous (IV)] routes.

The dose of rAAV to be administered in methods disclosed herein will vary depending, for example, on the particular rAAV, the mode of administration, the treatment goal, the individual, and the cell type(s) being targeted, and may be determined by methods standard in the art. More than one dose may be administered, for example, one, two, three or more doses. Titers of rAAV in a dose may range from about $1\times10^6$, about $1\times10^7$, about $1\times10^8$, about $1\times10^9$, about $1\times10^{10}$, about $1\times10^{11}$, about $1\times10^{12}$, about $1\times10^{13}$, about $1\times10^{14}$, or to about $1\times10^{15}$ or more DNase resistant particles (DRP) per ml. Dosages may also be expressed in units of viral genomes (vg) (i.e., $1\times10^7$ vg, $1\times10^8$ vg, $1\times10^9$ vg, $1\times10^{10}$ vg, $1\times10^{11}$ vg, $1\times10^{12}$ vg, $1\times10^{13}$ vg, $1\times10^{14}$ vg, $1\times10^{15}$ respectively). Methods for titering AAV are described in Clark et al., *Hum. Gene Ther.*, 10: 1031-1039 (1999).

In some embodiments of the foregoing methods in which the route of administration is an IM route, the dose of the rAAV administered is from about $3\times10^{11}$ to at least about $5\times10^{12}$ vg/injection. (All ranges herein are intended to represent each individual value in the ranges, as well as the individual upper and lower values of each range.) In some embodiments of the foregoing methods in which the route of administration is an IM route, the dose of the rAAV administered is $3\times10^{11}$ vg/injection. In some embodiments of the foregoing methods in which the route of administration is an IM route, the dose of the rAAV administered is $1\times10^{12}$ vg/injection. In some embodiments of the foregoing methods in which the route of administration is an IM route, the dose of the rAAV administered is $5\times10^{12}$ vg/injection.

In some embodiments of the foregoing methods in which the route of administration is an ILP route, the dose of the rAAV administered is from about $6\times10^{12}$ to at least about $4.8\times10^{13}$ vg/kg. (All ranges herein are intended to represent each individual value in the ranges, as well as the individual upper and lower values of each range.) In some embodiments of the foregoing methods in which the route of administration is ILP, the dose of the rAAV administered is $6\times10^{12}$ vg/kg/limb. In some embodiments of the foregoing methods in which the route of administration is ILP, the dose of the rAAV administered is $1.2\times10^{13}$ vg/kg/limb. In some embodiments of the foregoing methods in which the route of administration is ILP, the dose of the rAAV administered is $2.4\times10^{13}$ vg/kg/limb. In some embodiments of the foregoing methods in which the route of administration is ILP, the dose of the rAAV administered is $4.8\times10^{13}$ vg/kg/limb.

In some embodiments of the foregoing methods in which the route of administration is a systemic IV route, the dose of the rAAV administered is from about $2\times10^{14}$ to at least about $6\times10^{15}$ vg/kg. In some embodiments of the foregoing methods in which the route of administration is a systemic IV route, the dose of the rAAV administered is from about $4\times10^{14}$ to at least about $6\times10^{15}$ vg/kg. (All ranges herein are intended to represent each individual value in the ranges, as well as the individual upper and lower values of each range.) In some embodiments of the foregoing methods in which the route of administration is systemic IV administration, the dose of the rAAV administered is $4\times10^{14}$ vg/kg. In some embodiments of the foregoing methods in which the route of administration is systemic IV administration, the dose of the rAAV administered is $8\times10^{14}$ vg/kg. In some embodiments of the foregoing methods in which the route of administration is systemic IV administration, the dose of the rAAV administered is $2\times10^{15}$ vg/kg. In some embodiments of the foregoing methods in which the route of administration is systemic IV administration, the dose of the rAAV administered is $6\times10^{15}$ vg/kg.

Human patients are subjects contemplated herein for treatment. Human patients are subjects contemplated herein for treatment by IM delivery. Such patients include those patients that, e.g.: (i) are 9 years of age or older, (ii) are male, (iii) are ambulant or non-ambulant; (iv) have a confirmed mutation in the DMD gene using a clinically accepted technique that defines the mutation; (v) by magnetic resonance imaging of the extensor digitorum *brevis* (EDB) muscle show a preservation of sufficient muscle mass to permit transfection or gene transfer; (vi) are of any ethnic group; (vii) have the ability to cooperate with all study procedures; (viii), if appropriate, and sexually mature and/or active, are willing to practice a reliable method of contraception; and/or (ix) are receiving a stable dose of corticosteroid therapy (e.g., deflazacort, prednisone, or a generic form thereof) for at least 12 weeks prior to gene transfer. Suitable patients may not include, e.g., those: (i) with active viral infections based on clinical observation; (ii) who have a DMD mutation without weakness or loss of function; (iii) with symptoms of cardiomyopathy, such as dyspnea on exertion, pedal edema, shortness of breath upon lying flat, or rales at the base of the lung; (iv) who, by echocardiogram, have an ejection fraction below about 40%; (v) with serological evidence of infection with HIV or Hepatitis A, B, or C; (vi) who have or have been diagnosed as having (or are being treated for) an autoimmune disease; (vii) who have persistent leukopenia or leukocytosis (white blood cell count ≤3.5 K/µL or ≥20.0 K/µL) or an absolute neutrophil count <1.5 K/µL; (viii) who have a concomitant illness or requirement for chronic drug treatment that in the opinion of a medical practitioner creates an unnecessary risk for gene transfer; (ix) who have an rAA Vrh74 binding antibody titer of ≥1:400 as determined by an ELISA immunoassay; or (x) have the presence of circulating anti-Sda antibodies. In an exemplary clinical protocol, DMD patients receive bilateral injections with one extensor digitorum *brevis* (EDB) muscle of each patient receiving the vector rAAVrh74.MCK.GALGT2 and the other EDB muscle of each patient receiving saline alone. Subjects receive a dose of vector of $1\times10^{12}$ vg (total dose).

Cell transduction efficiencies of the methods described above and below may be at least about 60, 65, 70, 75, 80, 85, 90, or 95 percent. In some embodiments involving IV limb perfusion delivery, transduction efficiency is increased by increasing the volume of the composition in which the rAAV is delivered, pre-flushing before delivery of the rAAV and/or increasing dwell time of the rAAV.

In another aspect, rAAV genomes are provided herein. The genomes of the rAAV administered comprise a GALGT2 polynucleotide under the control of transcription control sequences. The rAAV genomes lack AAV rep and cap DNA. AAV DNA in the rAAV genomes may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10, AAV-11 and AAVrh.74. The nucleotide sequences of the genomes of these AAV serotypes are known in the art as noted in the Background Section above. In some embodiments, the AAV DNA in the rAAV genomes is from AAV rh.74. The polynucleotide sequence of the AAV rh. 74 genome is set out in SEQ ID NO: 1, wherein nucleotides 210-2147 are the Rep 78 gene open reading frame, 882-208 are the Rep52 open reading frame, 2079-2081 are the Rep78 stop, 2145-2147 are the Rep78 stop, 1797-1800 are a splice donor site, 2094-2097 are a splice acceptor site, 2121-2124 are a splice acceptor site, 174-181 are the p5 promoter +1 predicted, 145-151 are the p5 TATA box, 758-761 are the p19 promoter +1 predicted, 732-738 are the p19 TATA box, 1711-1716 are the p40 TATA box, 2098-4314 are the VP1 Cap gene open reading frame, 2509-2511 are the VP2 start, 2707-2709 are the VP3 start and 4328-4333 are a polyA signal.

In some embodiments, the transcription control sequences of the rAAV genomes are muscle-specific control elements, including, but not limited to, those derived from the actin and myosin gene families, such as from the myoD gene family [See Weintraub et al., *Science,* 251: 761-766 (1991)], the myocyte-specific enhancer binding factor MEF-2 [Cserjesi and Olson, *Mol. Cell. Biol.,* 11: 4854-4862 (1991)], control elements derived from the human skeletal actin gene [Muscat et al., *Mol. Cell. Biol.,* 7: 4089-4099 (1987)], the cardiac actin gene, muscle creatine kinase (MCK) promoter [Johnson et al., *Mol. Cell. Biol.,* 9:3393-3399 (1989)] and the MCK enhancer, MHCK7 promoter (a modified version of MCK promoter that incorporates an enhancer from myosin heavy chain [Salva et al., *Mol. Ther.,* 15: 320-329 (2007)]), desmin promoter, control elements derived from the skeletal fast-twitch troponin C gene, the slow-twitch cardiac troponin C gene and the slow-twitch troponin I gene: hypozia-inducible nuclear factors [Semenza et al., *Proc. Natl. Acad. Sci. USA,* 88: 5680-5684 (1991)], steroid-inducible elements and promoters including the glucocorticoid response element (GRE) [See Mader and White, *Proc. Natl. Acad. Sci. USA,* 90: 5603-5607 (1993)], and other control elements. In some embodiments, the transcription control elements include the MCK promoter. In some embodiments, the transcription control elements include the MHCK7 promoter.

In some embodiments, the GALGT2 polynucleotide in a rAAV genome is the GALGT2 cDNA set out in Genbank Accession #AJ517771 (set out as nucleotides 1002-2522 of SEQ ID NO: 2). In some embodiments, the GALGT2 polynucleotide in a rAAV genome is the GALGT2 cDNA set out in Genbank Accession #AJ517771, or is a variant polynucleotide having 80%, 81%, 82%, 83%, 84%, 85%, 86%, 87%, 88%, 89%, 90%, 91%, 92%, 93%, 94%, 95%, 96%, 97%, 98% or 99% sequence identity to the GALGT2 cDNA. In some embodiments, the variant GALGT2 polynucleotide encodes the same GALGT2 polypeptide as the polypeptide encoded by GALGT2 cDNA set out in Genbank Accession #AJ517771. The amino acid sequence of the GALGT2 polypeptide encoded by the GALGT2 cDNA set out in Genbank Accession #AJ517771 is set out in SEQ ID NO: 3. In some embodiments, the variant GALGT2 polynucleotide encodes a variant GALGT2 polypeptide with at least one amino acid sequence alteration as compared to the amino acid sequence of the polypeptide (SEQ ID NO: 3) encoded by GALGT2 cDNA set out in Genbank Accession #AJ517771. An amino acid sequence alteration can be, for example, a substitution, a deletion, or an insertion of one or more amino acids, preferably conservative substitutions. A variant GALGT2 polypeptide can have any combination of amino acid substitutions, deletions or insertions where the glycosyltransferase activity of the polypeptide is retained. In one aspect, a variant GALGT2 polypeptide can have a number of amino acid alterations such that its amino acid sequence shares at least 60, 70, 80, 85, 90, 95, 97, 98, 99 or 99.5% identity with the amino acid sequence (SEQ ID NO: 3) encoded by GALGT2 cDNA set out in Genbank Accession #AJ517771.

In some embodiments, the rAAV genome is the MCK-.GALGT2 genome, the sequence of the GALGT2 gene cassette of which is set out in SEQ ID NO: 2 and is annotated as follows.

| STARTING NUCLEOTIDE | ENDING NUCLEOTIDE | NAME | DESCRIPTION |
|---|---|---|---|
| 53 | 230 | 5'ITR | Wild Type AAV2 inverted terminal repeat |
| 236 | 442 | MCK enhancer | Mouse muscle creatine kinase enhancer |
| 443 | 793 | MCK core promoter | Mouse muscle creatine kinase core promoter |
| 794 | 846 | Mu MCK Exon 1 | Native transcriptional start site of exon 1 of mouse MCK gene (untranslated) |
| 847 | 943 | SV40 intron | SV40 late 16S/19S splice donor and acceptor sites |
| 944 | 1000 | 5' untranslated region | 5' untranslated region from plasmid pCMVb |
| 1002 | 2522 | Human GALGT2 CDNA | Human GALGT2 cDNA |
| 2531 | 2579 | Syn pA | Artificial polyadenylation signal |
| 2581 | 2762 | 3' ITR | Wild Type AAV2 inverted terminal repeat |

In yet another aspect, an isolated nucleic acid comprising the nucleotide sequence depicted in SEQ ID NO: 2 is provided. In some embodiments, the isolated nucleic acid consists of the nucleotide sequence depicted in SEQ ID NO: 2.

Also provided is an isolated nucleic acid comprising, in order from 5' to 3': (i) a first AAV2 inverted terminal repeat sequence (ITR); (ii) a muscle creatine kinase promoter sequence; (iii) a nucleotide sequence encoding a human GALGT2 polypeptide; and (iv) a second AAV2 ITR sequence, wherein the human GALGT2 polypeptide has an amino acid sequence that is at least 90% identical to SEQ ID NO:3, is 100% identical to SEQ ID NO:3, or is encoded by nucleotides 1002-2522 of SEQ ID NO: 2.

Recombinant AAV comprising the foregoing nucleic acids are contemplated as well as rAAV comprising a nucleotide sequence that is at least 90% identical to the nucleotide sequence depicted in SEQ ID NO:2.

DNA plasmids comprising rAAV genomes of the disclosure are provided. The DNA plasmids comprise rAAV genomes contemplated herein. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11 and AAV rh74. Production of pseudotyped rAAV is disclosed in, for example, WO 01/83692. Other types of rAAV variants, for example rAAV with capsid mutations, are also contemplated. See, for example, Marsic et al., *Molecular Therapy*, 22(11): 1900-1909 (2014).

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, *Proc. Natl. Acad. S6. USA*, 79:2077-2081), addition of synthetic linkers containing restriction endonuclease cleavage sites (Laughlin et al., 1983, *Gene*, 23:65-73) or by direct, blunt-end ligation (Senapathy & Carter, 1984, *J. Biol. Chem.*, 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells. Methods for producing rAAV with self-complementary genomes are also known in the art.

General principles of rAAV production are reviewed in, for example, Carter, 1992, *Current Opinions in Biotechnology*, 1533-539; and Muzyczka, 1992, *Curr. Topics in Microbial. and Immunol.*, 158:97-129). Various approaches are described in Ratschin et al., *Mol. Cell. Biol.* 4:2072 (1984); Hermonat et al., *Proc. Natl. Acad. Sci. USA*, 81:6466 (1984); Tratschin et al., *Mol. Cell. Biol.* 5:3251 (1985); Mclaughlin et al., *J. Virol.*, 62:1963 (1988); and Lebkowski et al., 1988 *Mol. Cell. Biol.*, 7:349 (1988). Samulski et al. (1989, *J. Virol.*, 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) *Vaccine*

13:1244-1250; Paul et al. (1993) *Human Gene Therapy* 4:609-615; Clark et al. (1996) *Gene Therapy* 3:1124-1132; U.S. Pat. Nos. 5,786,211; 5,871,982; and 6,258,595. The foregoing documents are hereby incorporated by reference in their entirety herein, with particular emphasis on those sections of the documents relating to rAAV production.

In a further aspect, the disclosure thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

The rAAV may be purified by methods standard in the art such as by column chromatography or cesium chloride gradients. Methods for purifying rAAV vectors from helper virus are known in the art and include methods disclosed in, for example, Clark et al., *Hum. Gene Ther.,* 10(6): 1031-1039 (1999); Schenpp and Clark, *Methods Mol. Med.,* 69 427-443 (2002); U.S. Pat. No. 6,566,118 and WO 98/09657.

Thus, in another aspect, the disclosure contemplates a rAAV comprising a GALGT2 polynucleotide. In some embodiments, the rAAV comprises AAV rh74 capsid and a GALGT2 polynucleotide. In some embodiments, the genome of the rAAV lacks AAV rep and cap DNA. In some embodiments of the methods, the rAAV is rAAVrh74.MCK.GALGT2. In some embodiments, the rAAV is a self-complementary genome.

In another aspect, the disclosure contemplates compositions comprising a rAAV described herein. Compositions of the disclosure comprise rAAV in a pharmaceutically acceptable carrier. The compositions may also comprise other ingredients such as diluents. Acceptable carriers and diluents are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG). In some embodiments, the rAAV is formulated in Tris, $MgCl_2$, NaCl and pluronic F68. In some embodiments, the rAAV is formulated in 20 mM Tris (pH 8.0), 1 mM $MgCl_2$ and 200 mM NaCl containing 0.001% pluronic F68.

Combination treatments are also contemplated herein. Combinations as used herein include simultaneous treatment or sequential treatments. Combinations of methods of the disclosure with standard medical treatments (e.g., corticosteroids and/or immunosuppressive drugs) are specifically contemplated, as are combinations with novel treatments. In various embodiments, subjects are treated with corticosteroids before, during or after (or with any permutation of combinations of two or more of the three possibilities), the subject is treated according to a method contemplated herein.

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

DESCRIPTION OF DRAWING

FIG. 1 provides a schematic of The rAAVrh74.MCK.GALGT2 gene cassette described in Example 1.

EXAMPLES

Thus, aspects and embodiments of the invention are illustrated by the following examples.

Example 1

A non-replicating rAAV termed rAAVrh74.MCK.GALGT2 was generated. The rAAV vector contains the complete human GALGT2 cDNA (Genbank Accession #AJ517771) under the control of a muscle creatine kinase promoter (MCK; a muscle specific promoter). A MCK promoter/enhancer sequence was used to drive muscle-specific gene (expression and is composed of the mouse MCK core enhancer (206 bp) fused to the 351 bp MCK core promoter (proximal). After the core promoter, the 53 bp endogenous mouse MCK Exon1 (untranslated) is present for efficient transcription initiation, followed by the SV40 late 16S/19S splice signals (97 bp) and a small 5'UTR (61 bp). The intron and 5' UTR are derived from plasmid pCMVß (Clontech). The GALGT2 cassette has a consensus Kozak sequence immediately in front of the ATG start and a small 53 bp synthetic polyA signal for mRNA termination. The human GALGT2 cassette was previously described by Martin et al (2009), supra. The only viral sequences included are the inverted terminal repeats (ITR) of AAV2, which are required for both viral DNA replication and packaging. The pAAVrh74.MCK.GALGT2 plasmid contains the human GALGT2 cDNA expression cassette flanked by AAV2 inverted terminal repeat (ITR) sequences. The gene cassette includes an MCK promoter, a chimeric intron with a Kozak sequence for optimizing gene expression, human GALGT2 coding sequences and a polyA signal (see FIG. 1). The sequence of the gene cassette with flanking AAV ITRs is set out in SEQ ID NO: 2.

The AAV vectors including the GALGT2 polynucleotides were produced by a modified cross-packaging approach in an adenovirus-free, triple plasmid DNA transfection (CaPO4 precipitation) method in HEK293 cells [Rabinowitz et al., *J. Virol.,* 76:791-801 (2002)]. Vector was produced by co-transfecting plasmid containing GALGT2 polynucleotide with an AAV helper plasmid rep2-cap rh.74 and an adenovirus helper plasmid in similar fashion as that previously described [Wang et al., *Gene. Ther.,* 10:1528-1534 (2003)]. Plasmid rep2-cap rh. 74 encodes the wild-type AAV2 rep gene and rh.74 cap gene, and the adenovirus helper plasmid (pAdhelper) expresses the adenovirus type 5 E2A, E4ORF6, and VA I/II RNA genes which are required for high-titer rAAV production.

Vectors were purified from clarified 293 cell lysates by sequential iodixanol gradient purification and anion-exchange column chromatography using a linear NaCl salt gradient as previously described [Clark et al., *Hum. Gene Ther*, 10:1031-1039 (1999)]. Vector genome (vg) titers were measured using QPCR based detection with a MCK specific primer/probe set and utilized the Prism 7500 Taqman detector system (PE Applied Biosystems) as previously described (Clark et al., supra). Vector stock titers ranged between $1-40 \times 10^{12}$ vg/mL.

The vector is formulated in 20 mM Tris (pH 8.0), 1 mM $MgCl_2$ and 200 mM NaCl containing 0.001% pluronic F68. The vector is supplied as a frozen liquid that is thawed before clinical administration.

Example 2

IM Delivery to Subjects with DMD

Human patients are subjects contemplated herein for treatment by IM delivery. In an exemplary clinical protocol, DMD patients receive bilateral injections with one extensor digitorum *brevis* (EDB) muscle of each patient receiving the vector rAAVrh74.MCK.GALGT2 and the other EDB muscle of each patient receiving saline alone. Subjects in a first cohort receive a low dose of vector of $3 \times 10^{11}$ vg (total dose). Subjects in a second cohort receive a higher dose of vector of $1 \times 10^{12}$ vg (total dose).

Immediately prior to transportation to the clinical setting, appropriate dilutions of the vector are prepared. The dilution for the injection is 1:1 with normal saline. The vector is kept on ice (not frozen) until administration and is administered to the subject within 8 hours of preparation. Handling of rAAVrh74.MCK.GALGT2 follows compliance standards for Biosafety Level 1 vectors. See, www4.od.nih.gov/oba/RAC/guidelines_02/APPENDIX_G.htm#Toc7246561.

Subjects have muscle weakness by clinical exam. The genetic diagnosis of DMD is established on the basis of a DMD gene mutation consistent with DMD, in the setting of an appropriate clinical history. In this study, all subjects are non-ambulant, having lost ambulation in an age range diagnostic of DMD (i.e., less than 12 years old without steroid therapy, or less than 15 years old in the setting of longstanding steroid treatment). Subjects receive a stable dose of corticosteroid therapy (either prednisone or deflazacort, or their generic forms) for twelve weeks prior to treatment.

The vector or control is delivered via direct intramuscular injection into the extensor digitorum *brevis* (EDB) muscle of one foot of a subject, while the other foot receives saline alone. Conscious sedation is used on participants under 12 years of age. Patients over 12 years of age may receive conscious sedation or a sedative (like lorazepam) at least one hour prior to gene transfer. In addition, the skin over the gene transfer site is pre-treated with a lidocaine/prilocaine eutectic mixture incorporated in a cream base (EMLA cream) or a cellulose disk (EMLA patch). Comparable cream-based anesthesia such as xylocaine cream may be used. Procedures are performed under sterile conditions. The injection site is cleansed with three successive applications of non-iodine containing surgical prep swabs and draped with disposable sterile drapes. A standard clinical Doppler ultrasound is used with a sterile sheath around the transducer to maintain asepsis of the injection field. For vector injections of rAAVrh74.MCK.GALGT2 or placebo to the EDB, disposable MyoJect Needles that enable simultaneous EMG recording and fluid injection are used to increase the precision of muscle injection. The anatomical midline point of the muscle is identified on the skin and 2 to 6 separate vector injections are distributed into the muscle. The injections are 0.5 cm in depth from the muscle surface. The total dose of vector is $3 \times 10^{11}$ vg in 1.5 ml in the low dose group and $1 \times 10^{12}$ vg in 1.5 ml in the high-dose group. The proximal and distal extent of vector delivery as determined by ultrasound is marked with an indelible radiographic marker for reference at the time of post-gene transfer muscle biopsy.

Subjects are followed with close monitoring of vital signs. Concomitant medications are monitored and documented after injection. Subjects are discharged two days after gene transfer (if no side effects are observed).

Subjects return for follow up visits. Muscle biopsies are conducted at day 45 or day 90. Immune studies at 45 and 75 days post-gene transfer and at 9, 12, 18, and 24 months include testing for binding antibody to rAAVrh74 and antibody to GALGT2, as well as ELISpot to detect T cell response to capsid antigens. Subjects are seen at the end of first and second years for a physical exam, strength testing and immune studies.

Example 3

Efficacy Outcome Measurements

Muscle biopsies are taken from EDB muscles. Samples are coded to maintain a blind in all subsequent analysis as to which was injected with rAAVrh74.MCK.GALGT2.

Efficacy outcome measures include: expression of GALGT2 as demonstrated with anti-CT epitope antibodies; GALGT2 protein expression quantified by western blot and assessed by densitometry; transduction efficiency measured by qPCR of the GALGT transgene from muscle, and expressed as vector genomes normalized to a genomic single-copy control; the number of fibers containing central nuclei compared between muscles by paired t-tests; and analyses will also include: Dystrophin expression (with antibodies to N-terminal, C-terminal, and rod domains), utrophin expression, and leukocyte markers including CD45, CD3, CD4, CD8, and MAC 387. Muscle is examined for histological appearance. Antibodies to rAAVrh74 along with PBMC ELISpots to both rAAVrh74 capsid and GALGT protein are evaluated at different time points during the study up to two years. The muscle analysis of gene expression and inflammation is also done without breaking the blind.

Transgene expression is compared blindly between both EDB muscles from a single subject, and between those subject's biopsies at day 45 or day 90. A vector-specific primer probe set is used to amplify a unique 5' untranslated leader sequence of the transgene that will distinguish transgene expressed GALGT2 protein from endogenous GALGT2. Quantification of protein is done using direct immunofluorescence (IF) and Western blot (WB) studies of muscle tissue. CD4+ and CD8+ mononuclear cells are quantified by immunostaining and reported as number of cells/mm2 area. MHCI and MHCII antigen expression are assessed on muscle sections. Muscle morphometrics are also be performed, including fiber size histograms and quantification of central nucleation. Analysis also includes PCR analysis for viral DNA.

Immune responses are assessed by IFN-γ ELISpots to GALGT2 and AAV capsid. A rise in IFN-γ of >2SD to either virus or transgene is considered significant. An additional measure of immune response is the binding antibody assay to AAV.

Measurements for improvements in one or more of absolute muscle specific force; force decrement during eccentric muscle contractions; serum CK level; serum cardiac troponin level; serum MMP9 level; grip strength; limb torque; limb mobility or flexibility; ambulation; 6 minute walk test; knee flexor or extensor strength; maximal voluntary isometric muscle contraction; North Star Ambulatory Assessment; muscle mass, fat reduction, or edema by limb T2-weighted MRI measures; muscle contractures; limb joint angle; heart function (heart rate, cardiac output, percent fractional shortening, stroke volume); respiration (including respiratory rate, blood oxygenation, need for supplemental oxygen); muscle necrosis; muscle regeneration; muscle wasting; muscle inflammation; muscle calcification; muscle central nucleation; muscle size or myofiber size; lifespan; and dystrophin or laminin alpha 2 surrogate protein expression (utrophin, plectin 1, laminin alpha 5, agrin) are among those contemplated. See, for example, Forbes et al., *Radiology*, 269(1): 198-207 (2013); Govoni et al., *Cell Mol. Life Sci.*, 70(23): 4585-4602 (2013); and Chandrasekharan and Martin, *Methods Enzymol.*, 479: 291-322 (2010).

For each of the measures, statistical analysis based on differences between pre- and post-gene transfer examinations (clinical, or on muscle biopsy) will be analyzed using a paired t test, with a p value of <0.05 indicating significance.

Example 4

Vascular Delivery by Isolated Limb Perfusion

A vascular delivery route termed isolated limb perfusion (ILP) is also contemplated for treatment of human patients. Multiple leg muscles can be targeted by ILP via delivery through the femoral artery. The method permits isolation of the limb from the general circulation, increasing transduction efficiency and preventing virus from escaping to the general circulation. [Rodino-Klapac et al., *Mol. Ther.*, 18: 109-117 (2010)]. An exemplary clinical protocol is set out below.

The rAAVrh74.MCK.GALGT2 is prepared as described in Examples 1 and 2.

The subject receives a stable dose of corticosteroid therapy (either prednisone or deflazacort, or their generic forms) for twelve weeks prior to treatment. Prednisone treatment is also continued after gene transfer. The sedated and anesthetized subject is secured to a surgical bed. Proximal and distal tourniquets are loosely positioned above the knee and below the gastrocemius muscle of a macaque. A small incision is placed at the femoral triangle and the femoral artery is identified and dissected free and looped with proximal and distal ligatures to control bleeding and facilitate catheter introduction. The femoral artery is cannulated with a 3.0 Fr introducer sheath via a modified Seldinger method by passing the pre-flushed sheath over a wire previously placed in the artery. The sheath is advanced only a few centimeters and secured in place with a 3.0 braided silk suture.

Following sheath placement in the femoral arteries and veins, 100-200 u/kg of unfractionated heparin is administered and allowed to circulate for 3-5 minutes. A Choice PT coronary guide wire is then placed initially into the right femoral vein and artery, and then ultimately into the left femoral vein and artery. A 4-mm diameter Tyshak Mini Balloon catheter is passed through the 3.3-French sheath through the right femoral artery into position in the femoral iliac artery junction. An 8-mm diameter×2 cm long Tyshak Mini Balloon catheter is passed through the 5-French sheath into appropriate position in the right femoral-iliac vein junction. Small hand injections of diluted contrast are performed to confirm appropriate blockage of both the left femoral artery and the right femoral vein. If needed, sheaths and ballons can be exchanged for larger sizes. For example, the 4-French sheath in the right femoral vein can be exchanged for a 6-French sheath and a 12 mm×2 cm long Tyshak II Balloon catheter can be passed over the Choice PT guidewire into appropriate position. Small hand injections through the side arm of the sheath are performed to confirm location and complete occlusion of the femoral vein.

A pre-flush of 2 mL/kg of Ringer's lactate heparinized solution is infused after both right femoral artery and femoral venous balloons are inflated, with isolation of the right leg. After 1 minute, the Ringer's lactate flush at 2 mL/kg is completed. Next, the rAAVrh74.MCK.GALGT2 vector is infused at a dose of between $2\times10^{12}$vg/kg/limb and $4.8\times10^{13}$vg/kg/limb in a volume of 8 mL/kg LR over 1-1/2 minutes (since bilateral limb perfusion is performed, leading to a total patient dose of between $4\times10^{12}$vg/kg and $9.6\times10^{13}$vg/kg). After the rAAVrh74.MCK.GALGT2 is delivered, there is 10 minutes of dwell time, and then the right femoral arterial sheath is then used to infuse 2 mL/kg of heparinized Ringer's lactate over 1 minute. The balloons are then deflated, and the catheters and guidewires are removed.

The left leg is then targeted for the same procedure. The left femoral artery is maintained with 3.3-French sheaths. Again, using a 4-mm diameter Tyshak Mini Balloon catheter in the left femoral artery over the Choice PT coronary guidewire, as well as the 12 mm×2 cm long Tyshak II Balloon catheter through the 5-French sheath in the left femoral vein with inflations up to 3 atmospheres of pressure, appropriate occlusion is demonstrated. The infusion protocol is repeated with 2 mL/kg of heparinized Ringer's lactate infused over 1 minute, and a dose of between $2\times10^{12}$vg/kg/limb and $4.8\times10^{13}$vg/kg/limb of rAAVrh74.MCK.GALGT2 is infused over 1 minute and 15 seconds, with the dwell time of 10 minutes. Finally, 2 mL/kg of heparinized Ringer's lactate is infused through left femoral arterial sheath, and then the sheaths are removed from all 4 access sites with pressure hemostasis and a HemCon patch.

Variations of this protocol can be used to deliver rAAVrh74.MCK.GALGT2 via other arteries to alternative groups of muscles as needed. For example, delivery via the phrenic, intercostal and/or subcostal arteries to supply the diaphragm muscle, or delivery via the coronary arteries to supply the heart are contemplated. Similar doses would be utilized for each procedure, and that multiple procedures might be done in a single patient or even in a single patient admission.

At the completion of dosing the tourniquets and catheter are removed and direct pressure is applied to the wound for 10 min to control bleeding. The wound is closed with a continuous subcuticular 4.0 Vicryl suture. A pressure dressing is applied to the site and kept in place until the subject awoke from anesthesia.

Following the ILP vector delivery protocol, subject follow up and efficacy outcome measurements/analyses similar to that described above for the IM-treated subjects are conducted.

Example 5

Systemic Vascular Delivery

Another contemplated route of delivery of the rAAVrh74.MCK.GALGT2 vector to muscle is systemic vascular delivery. An exemplary dose escalation study examining efficacy can be conducted as follows.

Determination of Dose Range

IV injection (via the tail vein) of $1.4 \times 10^{15}$ vg/kg rAAVrh74.MCK.GALGT2 at day 1 of age causes transduction of over 90% of all limb skeletal muscles in a wild type mouse, including tibialis anterior, gastrocnemius, quadriceps and triceps, and the same does leads to over 50% transduction of all cardiomyocytes in the wild type mouse heart and over 70% of cardiomyocytes in the heart of mdx model mice heart. Notably, analysis of overall mdx mouse heart function at 3 months after treatment, relative to mock-treated mdx control animals, showed almost a doubling of cardiac output as the result of rAAVrh74.MCK.GALGT2 treatment with this dose of vector, either with or without stimulation with dobutamine, a beta agonist that stimulates heart rate. Thus, there is an 80% increase in blood flow from the dystrophin-deficient heart after rAAVrh74.MCK.GALGT2 treatment when vector is given prior to the onset of disease-related cardiac pathology. $5 \times 10^{15}$ vg/kg is contemplated to be the maximal therapeutic dose to transduce all heart and skeletal muscle cells throughout the entire body using intravenous injection. Thus, it is contemplated that a dose range of about $5 \times 10^{13}$ vg/kg to about $5 \times 10^{15}$ vg/kg would cover the minimally effective dose and the optimally effective dose for rAAVrh74.MCK.GALGT2 treatment of the whole patient in a clinical IV study.

Protocol

The rAAVrh74.MCK.GALGT2 is prepared as described in Examples 1 and 2.

The subject is started on prophylactic enteral prednisolone (glucocorticoid) (approximately 1 mg/kg/day) one day prior to the rAAVrh74.MCK.GALGT2 administration. Prednisone treatment is also continued after gene transfer.

On the day of gene transfer (Day 0) prior to rAAVrh74.MCK.GALGT2 infusion, a physical exam is performed with vitals collected.

If a subject appears inadequately hydrated in the judgment of the PI, bolus(es) of 10-20 mL/kg normal saline may be given during the time between hospital admission and gene transfer. Subjects maintain their usual diet until eight hours prior to gene transfer, after which they have no solid food; clear liquids are allowed up until two hours prior to gene transfer, after which they will be fully NPO. They resume their usual PO intake after they return to pre-sedation baseline. Gene transfer will be performed under sterile conditions, under light to moderate sedation under the direction of a qualified anesthesiologist. Sedation may vary, but the subject can be sedated using inhaled nitrous prior to induction with propofol via an IV, and maintained with inhaled sevoflurane or a propofol drip. In those subjects who, in the opinion of the PI (and in consultation with the anesthesiologist), are determined to not need sedation in order to safely deliver the vector, sedation may be deferred.

All subjects in the trial receive an intravenous injection of rAAVrh74.MCK.GALGT2 via peripheral limb vein. The dose range contemplated is between $5 \times 10^{13}$ vg/kg and $5 \times 10^{15}$ vg/kg.

As one example, each vector dose is given undiluted, divided into 50 mL or less, to fill Becton Dickinson 60 mL capacity polypropylene syringes, prepared by the NCH Investigational Drug Pharmacy. The vector salt solution is approximately 400 mOsmol/L. Infusion is performed using a Smiths Medical Medfusion 4000 Syringe Infusion Pump with PharmGuard Infusion Management Software Suite, delivered via a Smiths Medical MX563 infusion tube. The infusion rate is not to exceed 2 ml/kg/min for any subject. The infusion is given over approximately 10 to 20 minutes. The vector is flushed from the infusion tubing using normal saline at the end of the infusion. It is contemplated that vector doses can be divided and administered differently as necessary.

Subjects are closely monitored for side effects during the infusion, including continuous heart rate, respiratory rate, and pulse oximetry; and intermittent blood pressure monitoring. Heart rate, respiratory rate, pulse oximetry, temperature, and blood pressure are measured before and immediately after the infusion, and every five minutes during the infusion, and repeated at 15 minutes post-infusion.

Subjects remain in an intensive care unit bed following gene transfer and remain admitted to the hospital for 48 hours after gene transfer. Vital signs are obtained hourly for 4 hours following the injection and then every 4 hours until discharge. Transfer out of intensive care may be undertaken after the initial 24 hours of post-infusion monitoring, if the PI has no concerns.

Following the vector delivery protocol, subject follow up and efficacy outcome analyses similar to that described above for the IM-treated subjects are conducted.

While the present invention has been described in terms of specific embodiments, it is understood that variations and modifications will occur to those skilled in the art. Accordingly, only such limitations as appear in the claims should be placed on the invention.

All documents referred to in this application are hereby incorporated by reference in their entirety with particular attention to the content for which they are referred. Also, this application claims the benefit of the filing date of U.S. Provisional Application Nos. 62/220,107 filed Sep. 17, 2015; 62/221,068 filed Sep. 20, 2015 and 62/301,260 filed February 2016; which are incorporated by reference in their entirety herein.

I claim:

1. A method of treating a Duchenne muscular dystrophy in a human subject in need thereof comprising the step of administering to the human subject a recombinant adeno-associated virus (rAAV), wherein the rAAV comprises a genome comprising a nucleic acid comprising, in order from 5' to 3':
    (i) a first AAV2 inverted terminal repeat sequence (ITR);
    (ii) muscle creatine kinase (MCK) enhancer comprising nucleotides 236-442 of SEQ ID NO: 2;
    (iii) a muscle creatine kinase core promoter sequence comprising nucleotides 443-793 of SEQ ID NO: 2;
    (iv) a nucleotide sequence encoding a human β1-4-N-acetyl-D-galactosamine glycosyltransferase (GALGT2) polypeptide; and
    (v) a second AAV2 ITR sequence;
    wherein the human GALGT2 polypeptide has an amino acid sequence that is at least 90% identical to SEQ ID NO: 3 or is 100% identical to SEQ ID NO: 3, or is encoded by a nucleotide sequence 90% identical to nucleotides 1002-2522 of SEQ ID NO: 2 or 100% identical to nucleotides 1002-2522 of SEQ ID NO: 2, and wherein the route of administration is intravascular administration.

2. The method of claim 1 wherein the route of administration is
    inter-arterial limb perfusion and the dose of the rAAV administered is about $6\times10^{12}$ vector genomes/kg/limb to about $4.8\times10^{13}$ vector genomes/kg/limb,
    inter-arterial limb perfusion and the dose of the rAAV administered is about $6\times10^{12}$ vector genomes/kg/limb,
    inter-arterial limb perfusion and the dose of the rAAV administered is about $1.2\times10^{13}$ vector genomes/kg/limb,
    inter-arterial limb perfusion and the dose of the rAAV administered is about $2.4\times10^{13}$ vector genomes/kg/limb, or
    inter-arterial limb perfusion and the dose of the rAAV administered is about $4.8\times10^{13}$ vector genomes/kg/limb.

3. The method of claim 1, wherein the nucleic acid further comprises 3' to said core promoter, a mouse MCK exon 1 sequence comprising nucleotides 794-846 of SEQ ID NO: 2.

4. The method of claim 3, wherein the nucleic acid further comprises 3' to said core promoter, an SV40 intron sequence comprising nucleotides 847-943 of SEQ ID NO: 2.

5. The method of claim 4, wherein the nucleic acid further comprises 3' to said core promoter, a 5' untranslated region comprising nucleotides 944-1000 of SEQ ID NO: 2.

6. The method of claim 5, wherein the nucleic acid further comprises 3' to said nucleotide sequence encoding a human GALGT2 polypeptide, a Syn pA synthetic polyadenylation signal sequence comprising nucleotides 2531-2579 of SEQ ID NO: 2.

7. The method of claim 6, wherein in the nucleic acid said first ITR comprises nucleotides 53-230 of SEQ ID NO: 2; and said second ITR comprises nucleotides 2581-2762 of SEQ ID NO: 2.

8. The method of claim 1, wherein in the nucleic acid said first ITR comprises nucleotides 53-230 of SEQ ID NO: 2, and/or said second ITR comprises nucleotides 2581-2762 of SEQ ID NO: 2.

9. The method of claim 1, wherein the rAAV comprises an rAAV.rh74.MCK.GALGT2 genome that is at least 90% identical to the nucleotide sequence of set out in SEQ ID NO: 2.

10. A method of claim 1, wherein the AAV comprises the rAAV.rh74.MCK.GALGT2 genome set out in SEQ ID NO: 2.

11. The method of claim 1, wherein the rAAV is administered as is a recombinant adeno-associated virus particle.

12. The method of claim 1, wherein the rAAV is serotype AAV-1, AAV-2, AAV-3, AAV-4, AAV-5, AAV-6, AAV-7, AAV-8, AAV-9, AAV-10, AAV-11, or AAVrh.74.

13. The method of claim 1, wherein the AAV DNA in the rAAV genome is from AAV rh.74.

14. The method of claim 13, wherein the polynucleotide sequence of the AAV rh.74 genome comprises the nucleotide sequence of SEQ ID NO: 1.

15. A method of treating Duchenne muscular dystrophy in a human subject in need thereof comprising the step of administering to the human subject a recombinant adeno-associated virus (rAAV), wherein the rAAV comprises a nucleic acid sequence having at least 90% identity to nucleotides 53 to 2762 of SEQ ID NO: 2, wherein the route of administration is intravascular administration.

16. The method of claim 15, wherein the rAAV is administered as is a recombinant adeno-associated virus particle.

17. The method of claim 15, wherein the rAAV is serotype AAV-1, AAV-2, AAV-3, AAV-4, AAV-5, AAV-6, AAV-7, AAV-8, AAV-9, AAV-10, AAV-11, or AAVrh.74.

* * * * *

SEQUENCE LISTING

<160> NUMBER OF SEQ ID NOS: 3

<210> SEQ ID NO 1
<211> LENGTH: 4472
<212> TYPE: DNA
<213> ORGANISM: Adeno-associated virus rh74

<400> SEQUENCE: 1

```
ctccatcact aggggtaacc gcgaagcgcc tcccacgctg ccgcgtcagc gctgacgtaa      60
attacgtcat aggggagtgg tcctgtatta gctgtcacgt gagtgctttt gcgacatttt     120
gcgacaccac gtggccattc atggtatata tggccgagtg agcgagcagg atctccattt     180
```

```
tgaccgcgaa atttgaacga gcagcagcca tgccgggctt ctacgagatc gtgcttaagg    240
tgccgagcga cctggacgag cacctgccgg gcatttctga ctcgtttgtg aactgggtgg    300
cagagaagga atgggagctg cccccggatt ctgacatgga tcggaatctg attgagcagg    360 caccccctgac cgtggccgag aagctacagc gcgacttcct ggtccaatgg cgccgcgtga   420
gtaaggcccc ggaggccctc ttctttgttc agttcgagaa gggcgagtcc tacttccacc    480
tccatattct ggtagagacc acggggggtca aatccatggt gctgggccgc ttcctgagtc   540
agattcggga caagctggtg cagaccatct accgcgggat cgagccgacc ctgcccaact    600
ggttcgcggt gacaaagacg cgtaatggcg ccggaggggg gaacaaggtg gtggacgagt    660
gctacatccc caactacctg ctgcccaaga ctcagcccga gctgcagtgg gcgtggacta    720
acatggagga gtatataagc gcgtgcttga acctggccga gcgcaaacgg ctcgtggcgc    780
agcacctgac ccacgtcagc cagacccagg agcagaacaa ggagaatctg aacccgaatt    840
ctgacgcgcc tgtcatccgg tcaaaaacct ccgcgcgcta catggagctg tcgggtggc    900 tggtggaccg gggcatcacc tccgagaagc agtggatcca ggaggaccag gcctcgtaca    960
tctccttcaa cgccgcctcc aactcgcggt ctcagatcaa ggccgcgctg acaatgccg    1020 gcaagatcat ggcgctgacc aaatccgcgc ccgactacct ggtaggcccc gctctgcccg    1080
cggacattaa atccaaccgc atctaccgca tcctggagct gaatggctac gaccctgcct    1140
acgccggttc cgtctttctc ggctgggccc agaaaaagtt tggcaaaagg aacaccatct    1200 ggctgttttgg gccggccacc acgggcaaga ccaacatcgc ggaagccatc gcccacgccg    1260
tgcccttcta cggctgcgtc aactggacca atgagaactt tcccttcaac gattgcgtcg    1320
acaagatggt gatctggtgg gaggagggca agatgacggc caaggtcgtg gagtccgcca    1380
aggccattct cggcggcagc aaggtgcgcg tggaccaaaa gtgcaagtcg tccgcccaga    1440
tcgatcccac ccccgtgatc gtcacctcca acaccaacat gtgcgccgtg attgacggga    1500
acagcaccac cttcgagcac cagcagccgt tgcaggaccg gatgttcaaa tttgaactta    1560
cccgccgtct ggagcacgac tttggcaagg tgacaaagca ggaagtcaaa gagttcttcc    1620
gctgggcgca ggatcacgtg accgaggtgg cgcatgagtt ctacgtcaga aagggtggag    1680
ctaacaaaag acccgccccc gatgacgcgg atataagcga gcccaagcgg gcctgcccct    1740
cagtcgcgga tccatcgacg tcagacgcgg aaggagctcc ggtggacttt gccgacaggt    1800
accaaaacaa atgttctcgt cacgcgggca tgcttcagat gctgtttccc tgcaaaacat    1860
gcgagagaat gaatcagaat ttcaacattt gcttcacgca cggaccagaa gactgttcag    1920
aatgtttccc tggcgtgtca gaatctcaac cggtcgtcag aaaaaagacg tatcggaaac    1980
tctgtgcgat tcatcatctg ctggggcggg cacccgagat tgcttgctcg gcctgcgacc    2040
tggtcaacgt ggacctggat gactgtgttt ctgagcaata aatgacttaa accaggtatg    2100
gctgccgatg gttatcttcc agattggctc gaggacaacc tctctgaggg cattcgcgag    2160
tggtgggacc tgaaacctgg agccccgaaa cccaaagcca accagcaaaa gcaggacaac    2220
ggccggggtc tggtgcttcc tggctacaag tacctcggac ccttcaacgg actcgacaag    2280
ggggagcccg tcaacgcggc ggacgcagcg gccctcgagc acgacaaggc ctacgaccag    2340
cagctccaag cgggtgacaa tccgtacctg cggtataatc acgccgacgc cgagtttcag    2400
gagcgtctgc aagaagatac gtcttttggg ggcaacctcg ggcgcgcagt cttccaggcc    2460
aaaaagcggg ttctcgaacc tctgggcctg gttgaatcgc cggttaagac ggctcctgga    2520
```

| | |
|---|---|
| aagaagagac cggtagagcc atcaccccag cgctctccag actcctctac gggcatcggc | 2580 |
| aagaaaggcc agcagcccgc aaaaaagaga ctcaattttg ggcagactgg cgactcagag | 2640 |
| tcagtccccg accctcaacc aatcggagaa ccaccagcag gcccctctgg tctgggatct | 2700 |
| ggtacaatgg ctgcaggcgg tggcgctcca atggcagaca ataacgaagg cgccgacgga | 2760 |
| gtgggtagtt cctcaggaaa ttggcattgc gattccacat ggctgggcga cagagtcatc | 2820 |
| accaccagca cccgcacctg ggccctgccc acctacaaca accacctcta caagcaaatc | 2880 |
| tccaacggga cctcgggagg aagcaccaac gacaacacct acttcggcta cagcaccccc | 2940 |
| tgggggtatt ttgacttcaa cagattccac tgccactttt caccacgtga ctggcagcga | 3000 |
| ctcatcaaca caactgggga ttccggcccc aagaggctca acttcaagct cttcaacatc | 3060 |
| caagtcaagg aggtcacgca gaatgaaggc accaagacca tcgccaataa ccttaccagc | 3120 |
| acgattcagg tctttacgga ctcggaatac cagctcccgt acgtgctcgg ctcggcgcac | 3180 |
| cagggctgcc tgcctccgtt cccggcggac gtcttcatga ttcctcagta cgggtacctg | 3240 |
| actctgaaca atggcagtca ggctgtgggc cggtcgtcct tctactgcct ggagtacttt | 3300 |
| ccttctcaaa tgctgagaac gggcaacaac tttgaattca gctacaactt cgaggacgtg | 3360 |
| cccttccaca gcagctacgc gcacagccag agcctggacc ggctgatgaa ccctctcatc | 3420 |
| gaccagtact tgtactacct gtcccggact caaagcacgg gcggtactgc aggaactcag | 3480 |
| cagttgctat tttctcaggc cgggcctaac aacatgtcgg ctcaggccaa gaactggcta | 3540 |
| cccggtccct gctaccggca gcaacgcgtc tccacgacac tgtcgcagaa caacaacagc | 3600 |
| aactttgcct ggacgggtgc caccaagtat catctgaatg gcagagactc tctggtgaat | 3660 |
| cctggcgttg ccatggctac ccacaaggac gacgaagagc gattttttcc atccagcgga | 3720 |
| gtcttaatgt ttgggaaaca gggagctgga aagacaacg tggactatag cagcgtgatg | 3780 |
| ctaaccagcg aggaagaaat aaagaccacc aacccagtgg ccacagaaca gtacggcgtg | 3840 |
| gtggccgata acctgcaaca gcaaaacgcc gctcctattg taggggccgt caatagtcaa | 3900 |
| ggagccttac ctggcatggt gtggcagaac cgggacgtgt acctgcaggg tcccatctgg | 3960 |
| gccaagattc tcatacggga cggcaacttt catccctcgc cgctgatggg aggctttgga | 4020 |
| ctgaagcatc cgcctcctca gatcctgatt aaaaacacac tgttcccgc ggatcctccg | 4080 |
| accaccttca ctaaggccaa gctggcttct ttcatcacgc agtacagtac cggccaggtc | 4140 |
| agcgtggaga tcgagtggga gctgcagaag gagaacagca aacgctggaa cccagagatt | 4200 |
| cagtacactt ccaactacta caaatctaca aatgtggact tgctgtcaa tactgagggt | 4260 |
| acttattccg agcctcgccc cattggcacc cgttacctca cccgtaatct gtaattacat | 4320 |
| gttaatcaat aaaccggtta attcgtttca gttgaacttt ggtctcctgt ccttcttatc | 4380 |
| ttatcggtta ccatagaaac tggttactta ttaactgctt ggtgcgcttc gcgataaaag | 4440 |
| acttacgtca tcgggttacc cctagtgatg ga | 4472 |

<210> SEQ ID NO 2
<211> LENGTH: 2762
<212> TYPE: DNA
<213> ORGANISM: Homo sapiens
<220> FEATURE:
<221> NAME/KEY: misc_feature
<223> OTHER INFORMATION: pAAV.MCK.GALGT2

<400> SEQUENCE: 2
gcccaatacg caaaccgcct ctccccgcgc gttggccgat tcattaatgc agctgcgcgc     60

-continued

```
tcgctcgctc actgaggccg cccgggcaaa gcccggggcgt cgggcgacct ttggtcgccc      120
ggcctcagtg agcgagcgag cgcgcagaga gggagtggcc aactccatca ctaggggttc      180
cttgtagtta atgattaacc cgccatgcta cttatctacg tagccatgct ctagacagcc      240
actatgggtc taggctgccc atgtaaggag gcaaggcctg ggacacccg agatgcctgg       300 ttataattaa cccagacatg tggctgctcc cccccccca acacctgctg cctgagcctc       360 accccaccc cggtgcctgg gtcttaggct ctgtacacca tggaggagaa gctcgctcta       420
aaaataaccc tgtccctggt gggctgtggg ggactgaggg caggctgtaa caggcttggg      480
ggccagggct tatacgtgcc tgggactccc aaagtattac tgttccatgt tcccggcgaa      540
gggccagctg tccccgcca gctagactca gcacttagtt taggaaccag tgagcaagtc      600
agcccttggg gcagcccata caaggccatg gggctgggca agctgcacgc ctgggtccgg      660
ggtgggcacg gtgcccgggc aacgagctga agctcatct gctctcaggg gcccctccct      720
ggggacagcc cctcctggct agtcacaccc tgtaggctcc tctatataac ccaggggcac      780
aggggctgcc cccgggtcac caccacctcc acagcacaga cagacactca ggagccagcc      840
agccaggtaa gtttagtctt tttgtctttt atttcaggtc ccggatccgg tggtggtgca      900
aatcaaagaa ctgctcctca gtggatgttg cctttacttc taggcctgta cggaagtgtt      960
acttctgctc taaaagctgc ggaattgtac ccgcggccgc gatgacttcg ggcggctcga     1020
gatttctgtg gctcctcaag atattggtca taatcctggt acttggcatt gttggattta    1080
tgttcggaag catgttcctt caagcagtgt tcagcagccc aagccagaa ctcccaagtc     1140 ctgccccggg tgtccagaag ctgaagcttc tgcctgagga acgtctcagg aacctctttt    1200
cctacgatgg aatctggctg ttcccgaaaa atcagtgcaa atgtgaagcc aacaaagagc     1260
agggaggtta caacttcag gatgcctatg gccagagcga cctcccagcg gtgaaagcga    1320
ggagacaggc tgaatttgaa cactttcaga ggagagaagg gctgccccgc ccactgcccc     1380
tgctggtcca gcccaacctc ccctttgggt acccagtcca cggagtggag gtgatgcccc     1440
tgcacacggt tcccatccca ggcctccagt ttgaaggacc cgatgccccc gtctatgagg     1500
tcaccctgac agcttctctg gggacactga acaccttgc tgatgtccca gacagtgtgg     1560
tgcagggcag aggccagaag cagctgatca tttctaccag tgaccggaag ctgttgaagt     1620
tcattcttca gcacgtgaca tacaccagca cggggtacca gcaccagaag gtagacatag     1680
tgagtctgga gtccaggtcc tcagtggcca gtttccagt gaccatccgc catcctgtca      1740
tacccaagct atacgaccct ggaccagaga ggaagctcag aaacctggtt accattgcta     1800
ccaagacttt cctccgcccc cacaagctca tgatcatgct ccggagtatt cgagagtatt     1860
acccagactt gaccgtaata gtggctgatg acagccagaa gccctggaa attaaagaca    1920 accacgtgga gtattacact atgcccttg ggaagggttg gtttgctggt aggaacctgg     1980
ccatatctca ggtcaccacc aaatacgttc tctgggtgga cgatgatttt ctcttcaacg    2040
aggagaccaa gattgaggtg ctggtggatg tcctggagaa aacagaactg gacgtggtag     2100
gcggcagtgt gctgggaaat gtgttccagt ttaagttgtt gctggaacag agtgagaatg     2160
gggcctgcct tcacaagagg atgggatttt tccaacccct ggatggcttc cccagctgcg     2220
tggtgaccag tggcgtggtc aacttcttcc tggcccacac ggagcgactc caaagagttg    2280
gctttgatcc ccgcctgcaa cgagtggctc actcagaatt cttcattgat gggctaggga     2340
ccctactcgt ggggtcatgc ccagaagtga ttataggtca ccagtctcgg tctccagtgg    2400
tggactcaga actggctgcc ctagagaaga cctacaatac ataccggtcc aacacctca     2460
```

```
cccgggtcca gttcaagctg gccctccact acttcaagaa ccatctccaa tgtgccgcat    2520
aagcggccgc aataaaagat ctttattttc attagatctg tgtgttggtt ttttgtgtgt    2580
ctagagcatg gctacgtaga taattagcat ggcgggttaa tcattaacta caaggaaccc    2640
ctagtgatgg agttggccac tccctctctg cgcgctcgct cgctcactga ggccgggcga    2700
ccaaaggtcg cccgacgccc gggctttgcc cgggcggcct cagtgagcga gcgagcgcgc    2760
ag                                                                   2762
```

<210> SEQ ID NO 3
<211> LENGTH: 506
<212> TYPE: PRT
<213> ORGANISM: Homo sapiens

<400> SEQUENCE: 3

```
Met Thr Ser Gly Gly Ser Arg Phe Leu Trp Leu Leu Lys Ile Leu Val
1               5                   10                  15

Ile Ile Leu Val Leu Gly Ile Val Gly Phe Met Phe Gly Ser Met Phe
            20                  25                  30

Leu Gln Ala Val Phe Ser Ser Pro Lys Pro Glu Leu Pro Ser Pro Ala
        35                  40                  45

Pro Gly Val Gln Lys Leu Lys Leu Leu Pro Glu Glu Arg Leu Arg Asn
    50                  55                  60

Leu Phe Ser Tyr Asp Gly Ile Trp Leu Phe Pro Lys Asn Gln Cys Lys
65                  70                  75                  80

Cys Glu Ala Asn Lys Glu Gln Gly Gly Tyr Asn Phe Gln Asp Ala Tyr
                85                  90                  95

Gly Gln Ser Asp Leu Pro Ala Val Lys Ala Arg Arg Gln Ala Glu Phe
            100                 105                 110

Glu His Phe Gln Arg Arg Glu Gly Leu Pro Arg Pro Leu Pro Leu Leu
        115                 120                 125

Val Gln Pro Asn Leu Pro Phe Gly Tyr Pro Val His Gly Val Glu Val
    130                 135                 140

Met Pro Leu His Thr Val Pro Ile Pro Gly Leu Gln Phe Glu Gly Pro
145                 150                 155                 160

Asp Ala Pro Val Tyr Glu Val Thr Leu Thr Ala Ser Leu Gly Thr Leu
                165                 170                 175

Asn Thr Leu Ala Asp Val Pro Asp Ser Val Val Gln Gly Arg Gly Gln
            180                 185                 190

Lys Gln Leu Ile Ile Ser Thr Ser Asp Arg Lys Leu Leu Lys Phe Ile
        195                 200                 205

Leu Gln His Val Thr Tyr Thr Ser Thr Gly Tyr Gln His Gln Lys Val
    210                 215                 220

Asp Ile Val Ser Leu Glu Ser Arg Ser Ser Val Ala Lys Phe Pro Val
225                 230                 235                 240

Thr Ile Arg His Pro Val Ile Pro Lys Leu Tyr Asp Pro Gly Pro Glu
                245                 250                 255

Arg Lys Leu Arg Asn Leu Val Thr Ile Ala Thr Lys Thr Phe Leu Arg
            260                 265                 270

Pro His Lys Leu Met Ile Met Leu Arg Ser Ile Arg Glu Tyr Tyr Pro
        275                 280                 285

Asp Leu Thr Val Ile Val Ala Asp Asp Ser Gln Lys Pro Leu Glu Ile
    290                 295                 300

Lys Asp Asn His Val Glu Tyr Tyr Thr Met Pro Phe Gly Lys Gly Trp
```

-continued

```
                305                 310                 315                 320
Phe Ala Gly Arg Asn Leu Ala Ile Ser Gln Val Thr Thr Lys Tyr Val
                    325                 330                 335

Leu Trp Val Asp Asp Phe Leu Phe Asn Glu Glu Thr Lys Ile Glu
                340                 345                 350

Val Leu Val Asp Val Leu Glu Lys Thr Glu Leu Asp Val Val Gly Gly
                355                 360                 365

Ser Val Leu Gly Asn Val Phe Gln Phe Lys Leu Leu Leu Glu Gln Ser
            370                 375                 380

Glu Asn Gly Ala Cys Leu His Lys Arg Met Gly Phe Phe Gln Pro Leu
385                 390                 395                 400

Asp Gly Phe Pro Ser Cys Val Val Thr Ser Gly Val Val Asn Phe Phe
                405                 410                 415

Leu Ala His Thr Glu Arg Leu Gln Arg Val Gly Phe Asp Pro Arg Leu
                420                 425                 430

Gln Arg Val Ala His Ser Glu Phe Phe Ile Asp Gly Leu Gly Thr Leu
                435                 440                 445

Leu Val Gly Ser Cys Pro Glu Val Ile Ile Gly His Gln Ser Arg Ser
            450                 455                 460

Pro Val Val Asp Ser Glu Leu Ala Ala Leu Glu Lys Thr Tyr Asn Thr
465                 470                 475                 480

Tyr Arg Ser Asn Thr Leu Thr Arg Val Gln Phe Lys Leu Ala Leu His
                485                 490                 495

Tyr Phe Lys Asn His Leu Gln Cys Ala Ala
                500                 505
```